(12) United States Patent
Ducharme et al.

(10) Patent No.: US 9,072,542 B2
(45) Date of Patent: Jul. 7, 2015

(54) SYSTEM AND METHOD FOR FIDUCIAL DEPLOYMENT

(75) Inventors: Richard W. Ducharme, Winston-Salem, NC (US); Vihar C. Surti, Winston-Salem, NC (US); Tyler E. McLawhorn, Winston-Salem, NC (US); Eugene Skelton, Dublin (IE); Martin J. Bruggeman, Dublin (IE)

(73) Assignee: Cook Medical Technologies LLC, Bloomington, IN (US)

( * ) Notice: Subject to any disclaimer, the term of this patent is extended or adjusted under 35 U.S.C. 154(b) by 952 days.

(21) Appl. No.: 12/964,062

(22) Filed: Dec. 9, 2010

(65) Prior Publication Data

US 2011/0152611 A1     Jun. 23, 2011

Related U.S. Application Data

(63) Continuation-in-part of application No. 12/764,432, filed on Apr. 21, 2010.

(60) Provisional application No. 61/287,964, filed on Dec. 18, 2009.

(51) Int. Cl.
*A61B 1/00* (2006.01)
*A61B 17/34* (2006.01)
(Continued)

(52) U.S. Cl.
CPC ......... *A61B 17/3468* (2013.01); *A61B 17/0401* (2013.01); *A61B 2018/00273* (2013.01);
(Continued)

(58) Field of Classification Search
CPC ............... A61B 19/54; A61B 17/0401; A61B 2019/5487; A61B 2018/00273; A61B 17/3468; A61B 2017/0649

USPC .......................................................... 600/426
See application file for complete search history.

(56) References Cited

U.S. PATENT DOCUMENTS 2,009,393 A   7/1935   Failla
3,470,834 A   10/1969  Bone
(Continued)

FOREIGN PATENT DOCUMENTS

EP   0093101 A2   11/1983
EP   1 518 549 A1   3/2005
(Continued)

OTHER PUBLICATIONS

PCT Notification of Transmittal of the International Search Report and the Written Opinion of the International Searching Authority, or the Declaration for PCT Application No. PCT/US2010/031842, date of mailing Nov. 3, 2010.
(Continued)

*Primary Examiner* — Vani Gupta
(74) *Attorney, Agent, or Firm* — Brinks Gilson & Lione

(57) ABSTRACT

Embodiments include a fiducial deployment system with a handle configured for actuation of same. A fiducial may include one or more protuberances configured to engage one or more slots in a needle of the system. The needle may be configured to deliver a plurality of fiducials to a target location in serial fashion, one at a time. In certain embodiments, echogenic placement of fiducials may present certain advantages. The handle may include structures configured for incrementally or otherwise controlledly deploying one or more fiducials by advancing a stylet through and/or retracting the body of a needle in which fiducials are disposed.

20 Claims, 23 Drawing Sheets

(51) Int. Cl.
- *A61B 19/00* (2006.01)
- *A61M 37/00* (2006.01)
- *A61B 17/04* (2006.01)
- *A61B 18/00* (2006.01)
- *A61B 17/064* (2006.01)
- *A61B 1/018* (2006.01)
- *A61B 17/00* (2006.01)
- *A61B 17/06* (2006.01)
- *A61N 5/10* (2006.01)

(52) U.S. Cl.
CPC ......... *A61B2017/0649* (2013.01); *A61B 1/018* (2013.01); *A61B 17/00234* (2013.01); *A61B 17/06166* (2013.01); *A61B 17/3478* (2013.01); *A61B 19/54* (2013.01); *A61B 2017/00407* (2013.01); *A61B 2017/0417* (2013.01); *A61B 2017/347* (2013.01); *A61B 2019/304* (2013.01); *A61B 2019/462* (2013.01); *A61B 2019/5408* (2013.01); *A61B 2019/5425* (2013.01); *A61B 2019/5487* (2013.01); *A61B 2019/5491* (2013.01); *A61M 37/0069* (2013.01); *A61N 5/1001* (2013.01); *A61N 5/1049* (2013.01)

(56) References Cited

U.S. PATENT DOCUMENTS

| | | | |
|---|---|---|---|
| 3,815,798 | A | 6/1974 | Lavitch et al. |
| 4,086,914 | A | 5/1978 | Moore |
| 4,105,030 | A | 8/1978 | Kercso |
| 4,700,692 | A | 10/1987 | Baumgartner |
| 4,716,901 | A | 1/1988 | Jackson et al. |
| 5,281,197 | A | 1/1994 | Arias et al. |
| 5,669,543 | A | 9/1997 | Ueno |
| 5,810,769 | A | 9/1998 | Schlegel et al. |
| 6,004,320 | A | 12/1999 | Casscells et al. |
| 6,283,948 | B1 | 9/2001 | McKernan et al. |
| 6,402,677 | B1 | 6/2002 | Jacobs |
| 6,450,938 | B1 | 9/2002 | Miller |
| 6,569,077 | B2 | 5/2003 | Schmidt |
| 6,824,507 | B2 | 11/2004 | Miller |
| 6,889,833 | B2 | 5/2005 | Seiler et al. |
| 7,083,566 | B2 | 8/2006 | Tornes et al. |
| 7,104,945 | B2 | 9/2006 | Miller |
| 7,144,386 | B2 | 12/2006 | Korkor et al. |
| 7,280,865 | B2 | 10/2007 | Adler |
| 7,361,135 | B2 | 4/2008 | Drobnik et al. |
| 7,429,240 | B2 | 9/2008 | Miller |
| 7,615,076 | B2 | 11/2009 | Cauthen, III et al. |
| 2003/0120141 | A1 | 6/2003 | Adler |
| 2003/0233101 | A1 | 12/2003 | Lubock et al. |
| 2003/0233126 | A1 | 12/2003 | Kaplan et al. |
| 2004/0260199 | A1* | 12/2004 | Hardia et al. .................. 600/566 |
| 2005/0038355 | A1 | 2/2005 | Gellman et al. |
| 2006/0058569 | A1 | 3/2006 | Chu |
| 2007/0270640 | A1 | 11/2007 | Dmitriou et al. |
| 2008/0287782 | A1 | 11/2008 | Traboulsi et al. |
| 2009/0105584 | A1 | 4/2009 | Jones |
| 2010/0063392 | A1* | 3/2010 | Nishina et al. ................ 600/439 |
| 2010/0137891 | A1 | 6/2010 | Shalon et al. |

FOREIGN PATENT DOCUMENTS

| | | |
|---|---|---|
| FR | 2 762 517 A1 | 4/1997 |
| JP | 6323312 A | 11/1994 |
| WO | WO 2009/100106 A1 | 8/2009 |
| WO | WO 2010/126750 A2 | 11/2010 |

OTHER PUBLICATIONS

*Gastroenterological Endoscopy* by Meinhard Classen, G.N.J. Tytgat, Charles J. Lightdale, p. 475.

*Fiducial Placement for Stereotatic Radiation by Using EUS: feasibility when using a marker compatible with a standard 22-gauge needle,* Tarek Amman, MD, Gregory A. Cote, MD, MS, Kimberly M. Creach, MD, Cara Kohlmeier, RDMS, Parag J. Parikh, MD, Riad R. Azar, MD; Gastrointestinal Endoscopy vol. 71, No. 3; 2010, pp. 630 and 633.

*EUS-guided fiducial placement for image-guided radiation therapy in GI malignancies by using a 22-gauge needle* (with videos); Christopher J. DiMaio, MD, Satish Nagula, MD, Karyn A. Goodman, MD, Alice Y. Ho, MD, Arnold J. Markowitz, MD, Mark A. Schattner, MD Hans Gerdes, MD; Gastrointestinal Endoscopy vol. 71, No. 7; 2010, pp. 1204-1210.

Ammar et al., "Fiducial placement for sterotactic radiation by using EUS: feasibility when using a marker compatible with a standard 22-gauge needle," Gastrointestinal Endoscopy, vol. 71, No. 3, pp. 630-633, www.giejournal.org., St. Louis, Missouri 2010.

Classen et al., "Gastroenterological Endoscopy," EUS-Guided Implantation of Radiopaque Markers (Fiducials), p. 475.

DiMaio et al., "EUS-guided fiducial placement for image-guided radiation therapy in GI malignancies by using a 22-gauge needle (with videos)," Gastrointestinal Endoscopy, vol. 71, No. 7, pp. 1204-1210.

International Search Authority for International Application No. PCT/US2010/059641, date mailed Mar. 21, 2011, 7 pages.

* cited by examiner

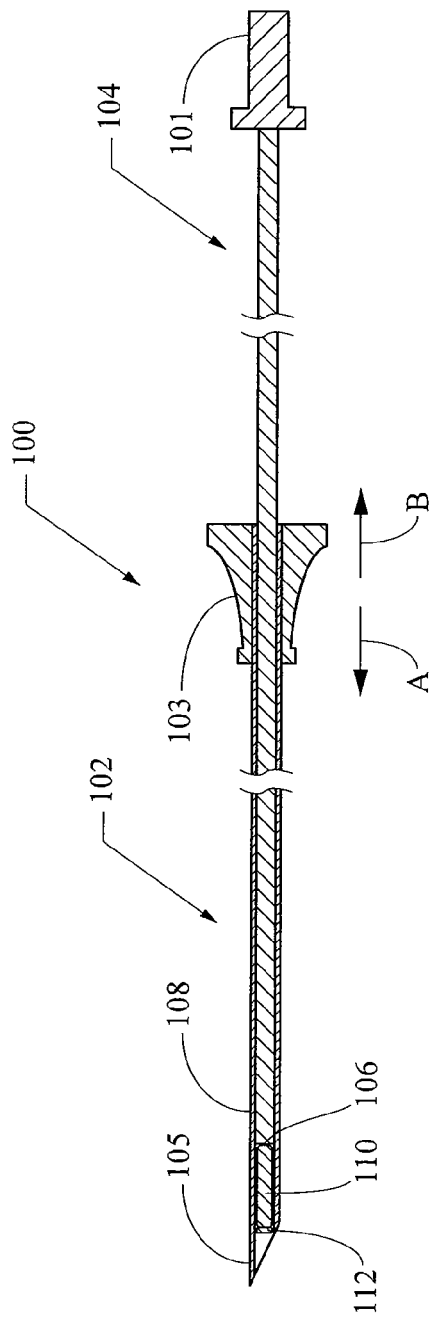
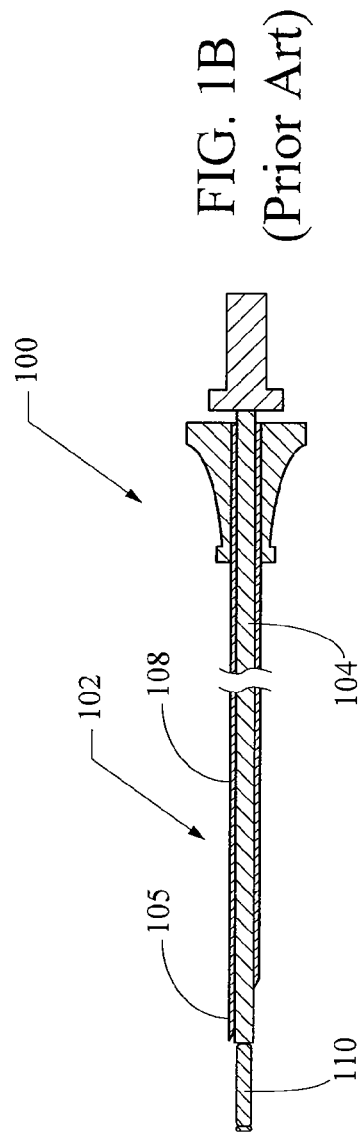
FIG. 1A (Prior Art)
FIG. 1B (Prior Art)

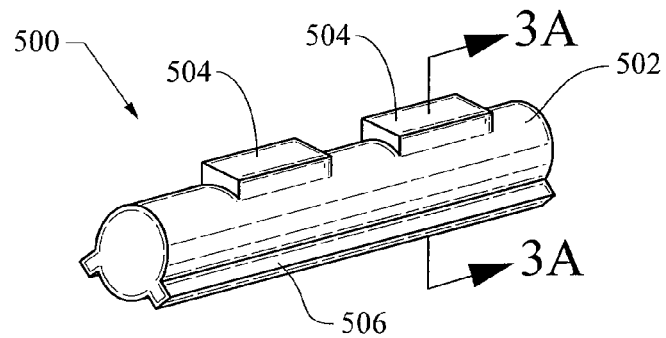
FIG. 3
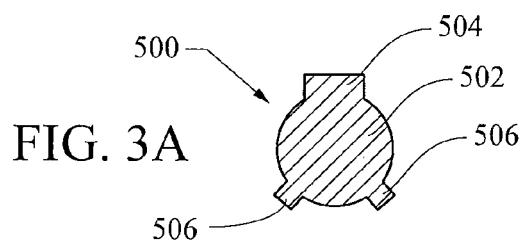
FIG. 3A
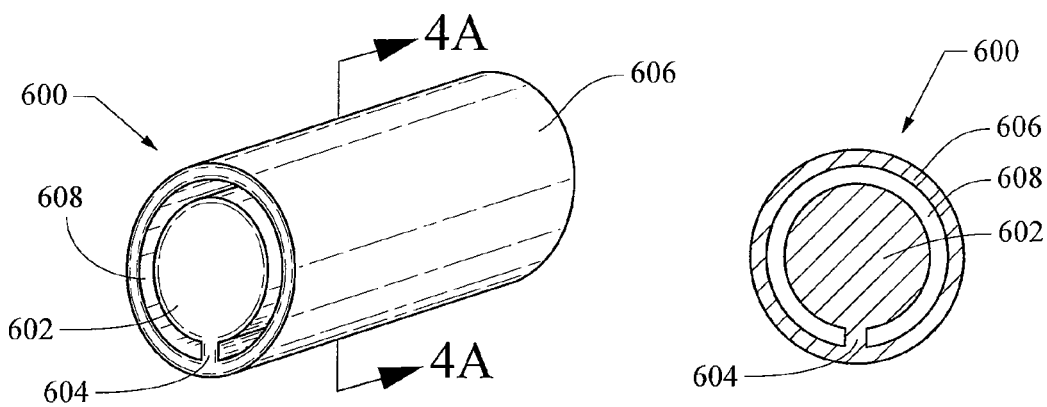
FIG. 4
FIG. 4A
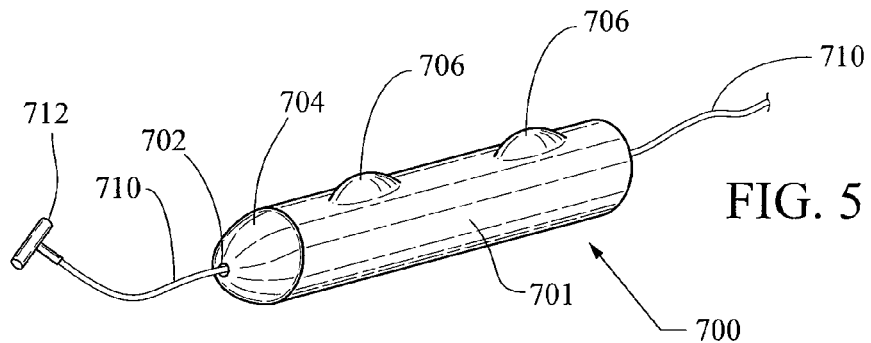
FIG. 5

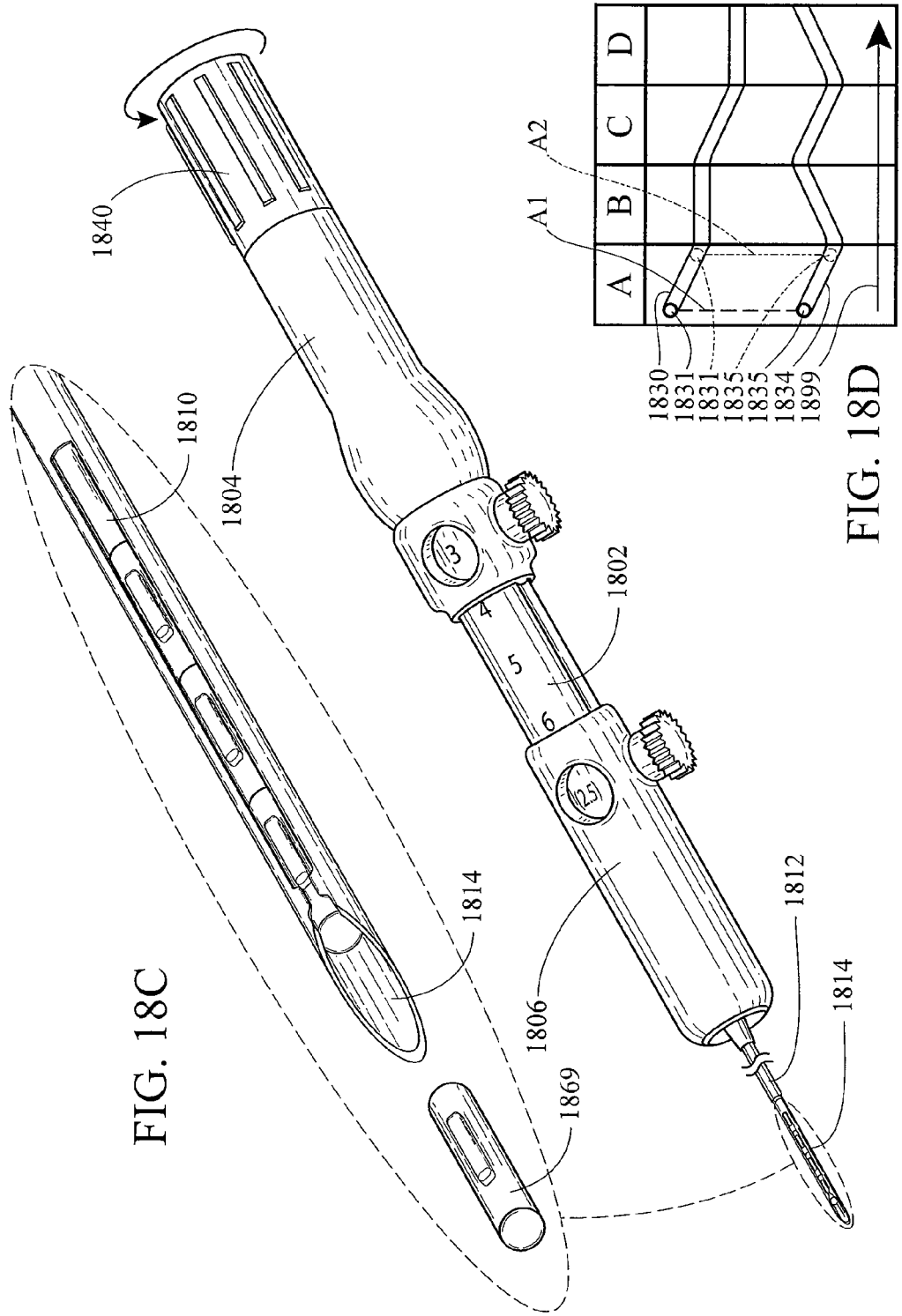

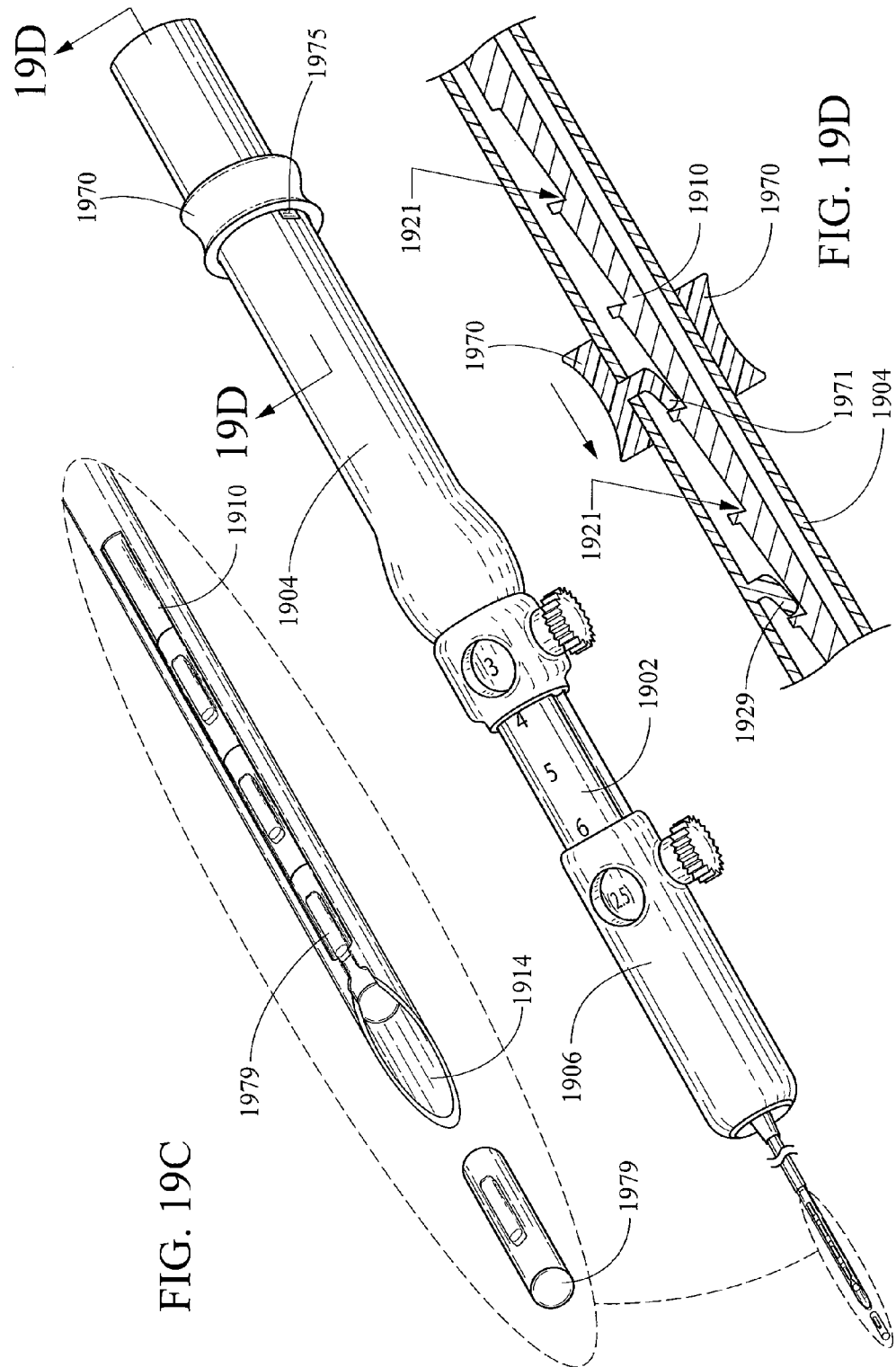

SYSTEM AND METHOD FOR FIDUCIAL DEPLOYMENT

CROSS-REFERENCE TO RELATED APPLICATIONS

This application claims priority to U.S. Provisional Patent Application No. 61/287,964, filed Dec. 18, 2009, and as a continuation-in-part of U.S. patent application Ser. No. 12/764,432, filed Apr. 21, 2010, each of which is incorporated herein by reference in its entirety.

TECHNICAL FIELD

The invention relates generally to a medical device system including one or more fiducials and methods of use for same. More particularly, the invention pertains to specially-configured fiducials, needles configured for use with them, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic gold markers—called fiducials—that can be used for targeting under ultrasound, MRI, x-ray, or other targeting techniques, which may be included in a treatment device).

A fiducial is typically formed of a radio-opaque material that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B). This causes the stylet 104 to push the seeds 110 out of the cannula 108. The procedure is then repeated to place other seeds/fiducials 110. When being used for targeting of radiation therapy, a minimum of three fiducials is typically required.

As will be appreciated from the disclosed structure, after deploying one fiducial, one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures or other access procedures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor.

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the external percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one at a time) rather than requiring manual reloading after placement of each fiducial.

BRIEF SUMMARY

Embodiments of a fiducial deployment system described herein may include one or more of: one or a plurality of fiducials having one or more protuberances, a slotted needle configured for delivering a plurality of fiducials in serial fashion, and a method of delivering fiducials to a target region.

BRIEF DESCRIPTION OF THE DRAWINGS

FIGS. 1A-1B show a prior art fiducial introducer and method of use.

FIGS. 3-3A show, respectively, a top perspective view and a transverse section view of a fourth embodiment of a fiducial;
FIGS. 4-4A show, respectively, a top perspective view and a transverse section view of a fifth embodiment of a fiducial;
FIG. 5 shows a sixth fiducial embodiment, including a suture along which the fiducial is slidably disposed;
FIGS. 11C-11D show two other methods of placing fiducials;
FIGS. 18A-18D show another advancement mechanism embodiment for a handle of a fiducial deployment system;
FIGS. 19A-19D show another advancement mechanism embodiment for a handle of a fiducial deployment system.

DETAILED DESCRIPTION

The terms "proximal" and "distal" are used herein in the common usage sense where they refer respectively to a handle/doctor-end of a device or related object and a tool/patient-end of a device or related object.

Figure 2A:
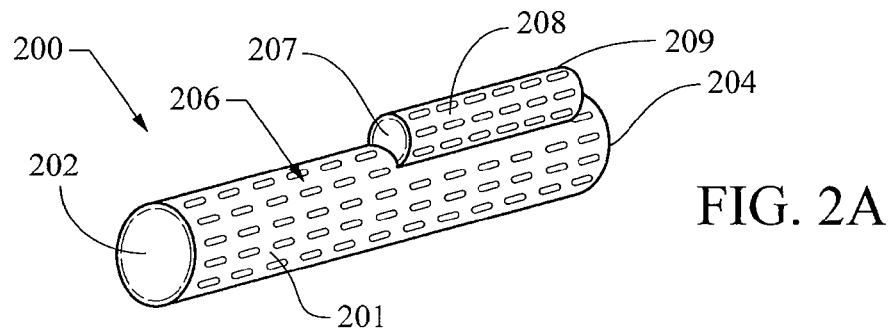
FIG. 2A shows a first embodiment of a fiducial.

Referring to FIG. 2A, a first embodiment of a fiducial 200 is described. The fiducial is configured for deployment in a patient body to be used for demarcating an internal body site. The fiducial 200 has a generally columnar body that is generally cylindrical with a generally circular transverse cross-section. A longitudinal surface face 206 of the body is shown as being dimpled to enhance its ability to reflect ultrasound waves and thereby provide a desirable echogenic profile. This dimpled characteristic may alternatively be embodied as a different irregular, patterned, or textured surface feature (e.g., knurled, ribbed) that may enhance the echogenicity of the fiducial 200, which will aid in visualizing it during EUS-guided placement, and allow it to be used in ultrasound visualization of a target site being marked by one or more fiducials 200 (e.g., a tumor). The fiducial 200 preferably will be formed of a radio-opaque, non-ferromagnetic material such as, for example, gold, platinum, palladium, iridium, or alloys thereof, with one preferred embodiment including an alloy of palladium with rhenium (advantages of which may include desirable radio-opacity, market-price stability superior to gold, and ultrasound-reflectivity/echogenicity due to density). Being radio-opaque will allow the fiducial to be used in deployment techniques using fluoroscopy, as well as making it detectable/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic construction of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography.

A protuberance 208 projects from the longitudinal face 206 of the fiducial body 201. The protuberance 208 has a distal protuberance end 207 corresponding to a distal body end 202, and proximal protuberance end 209 corresponding to a proximal body end 204. The distal and proximal body ends 202, 204 are each generally planar and transverse to the longitudinal axis. In this embodiment, the protuberance 208 is rounded and substantially parallel to the longitudinal central axis of the fiducial body, is only about one-half the length of the body 201, and is longitudinally located nearer the proximal end 204 than the distal end 204 of the body. In a preferred embodiment, the fiducial 200 is configured and dimensioned for passage through and release from a needle lumen. For an endoscopic delivery system, the fiducial body 201 (exclusive of the protuberance) preferably will have an outer diameter (OD) of about the same or less than the inner diameter (ID) of a needle lumen, but the OD of the fiducial body preferably will be no greater than the needle ID. As used herein, the OD of the fiducial refers to an imaginary circle (or other geometric shape) whose outermost boundaries all fit within the ID of the needle lumen. In other words, it is preferable that the fiducial is dimensioned to fit slidably into the needle lumen, except the protuberance, which projects into the slot.

The longer body portion distal of the protuberance can help make certain that, during deployment through a needle, a first fiducial distal of this second fiducial will be fully advanced out of the needle before that second fiducial is positioned for deployment, as will be made clearer with reference to FIGS. 7-11C below. Accordingly, in many preferred embodiments, the fiducial protuberance (of the second and successive fiducials) will be nearer its proximal end than its distal end, so that the distal fiducial body portion projects sufficiently distally that it will advance the preceding first fiducial completely out of the needle lumen by the time that the second fiducial is in a position to be deployed (see FIGS. 10-10A and corresponding text). It should be appreciated that, even if all surfaces of the central fiducial portion 201 and protuberance 208 are generally smooth, the preferred materials forming the fiducial 200 and the presence of the protuberance 208 may provide a desirable echogenic profile that is readily visualizable under ultrasound at a resolution sufficient for locating and/or navigating it in a patient's body.

Figure 2B:
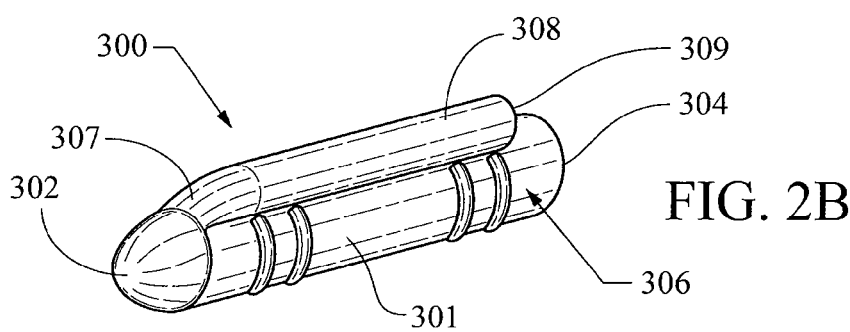
FIG. 2B shows a second embodiment of a fiducial.

FIG. 2B shows another embodiment of a fiducial 300. The fiducial 300 has a generally cylindrical body with a generally circular transverse cross-section. A longitudinal surface face 306 of the body 301 is shown as being ridged to enhance its ability to reflect ultrasound waves and thereby provide a desirable echogenic profile. This ridged characteristic may alternatively be embodied as a different non-smoothly-cylindrical or otherwise patterned surface feature (e.g., knurled, ribbed) that will enhance the echogenicity of the fiducial 300, which will aid in visualizing it during EUS-guided placement, and allow it to be used in ultrasound visualization of a target site being marked by one or more fiducials 300 (e.g., a tumor).

A protuberance 308 projects from the longitudinal face 306 of the fiducial body. The protuberance 308 has a distal protuberance end 307 that tapers down to a rounded distal body end 302, and proximal protuberance end 309 corresponding to a generally planar proximal body end 304. In this embodiment, the protuberance 308 is rounded and substantially parallel to the longitudinal central axis of the fiducial body, and it is about the same length as the body. In a preferred embodiment, the fiducial 300 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID.

Figure 2C:
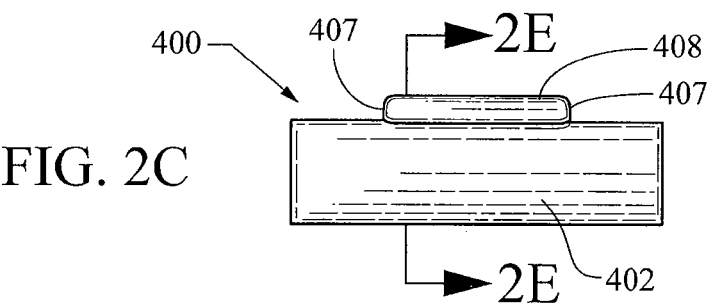
FIG. 2C-E show a third embodiment of a fiducial from, respectively, top, side, and transverse section views.
Figure 2D:
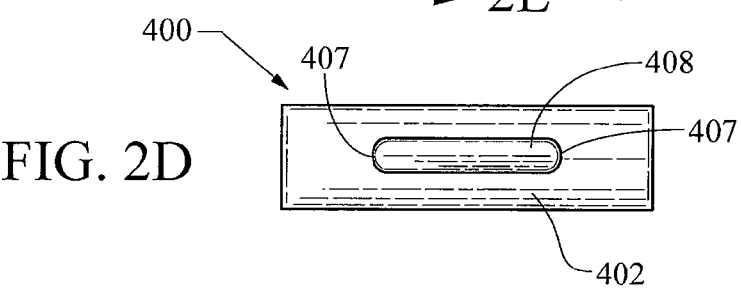
Figure 2E:
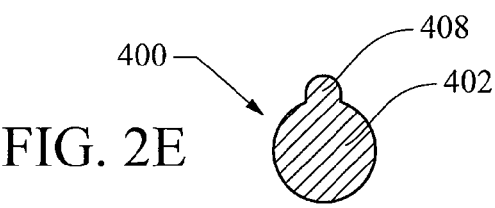

FIGS. 2C-2E show another embodiment of a fiducial 400. The fiducial 400 has a generally cylindrical body 402 formed as a mass with a generally circular transverse cross-section along its proximal and distal end sections. A protuberance 408 projects from the longitudinal circumferential face 406 of the fiducial body 402. As viewed from the top (shown in FIG. 2D), the protuberance 408 is generally obround. The irregular shape and increased surface area (as compared to a typical cylindrical fiducial) preferably enhances the echogenicity of the fiducial, which preferably will already be desirably high due in part to its composition.

The protuberance 408 includes protuberance end faces 407 that may provide one or more of chamfered, filleted, and radiused transition to the outer face 406 of the body 402. The body 402 is generally a right cylinder, but for the protuberance 408. In this embodiment, the protuberance 408 is rounded and substantially parallel to the longitudinal central axis of the fiducial body, and it is about one half the length of the body 402, and it is centered along the body length. In a preferred embodiment, the fiducial 400 is configured and dimensioned for passage through and release from a needle lumen. For an endoscopic delivery system, the fiducial body (exclusive of the protuberance) will have an outer diameter (OD) of about the same or less than the inner diameter (ID) of a needle lumen, but the fiducial body OD preferably will be no greater than the needle ID.

An exemplary embodiment is also described with reference to FIGS. 2C-2D. In one exemplary embodiment the body 402 is about 0.12 inches (3.05 mm) long and has an OD of about 0.034 inches (0.86 mm). The protuberance 408 is about 0.06 inches (1.5 mm) long and is aligned along a midline of the body. The protuberance 408 projects about 0.008 inches (0.2 mm) above the OD of the body 402 and is about 0.011 inches (0.28 mm) wide. These measurements and proportions may be varied in other embodiments while remaining within the scope of the presently-claimed material. For example, the protuberance may be more distally or proximally located, and may be at an angle relative to the midline such that it partially spirals around the outer surface of the body.

FIG. 2E shows an end view of a transverse section taken along line 2E-2E of FIG. 2C. It shows one embodiment of general proportions of a fiducial body and protuberance of the present system.

FIG. 3 shows an embodiment of a fiducial 500 that includes a plurality of protuberances. The fiducial 500 has a generally cylindrical body 502 with first and second parallel long protuberances 504 that extend most of the length of the body 500. The fiducial 500 also includes third and fourth short protuberances 506 that are longitudinally aligned with each other along the longitudinal axis of the body 502 and are also parallel with the ridge protuberances 504. As shown more clearly in FIG. 3A, which is a transverse section view along line 3A-3A of FIG. 3, the centerlines of the protuberances 504, 506 are shown as being generally equidistant (at about 60° from each other). It should be appreciated that the particular shapes, surface positions on fiducial bodies, and general proportions of these and the other protuberances disclosed herein may be interchanged or otherwise modified within the scope of the claims.

FIGS. 4 and 4A show another embodiment of a fiducial 600 that includes a generally cylindrical central body 602, a protuberance 604, and a columnar outer body 606 circumferentially encompassing most of the central body 602 in a manner forming a needle lumen 608. The protuberance connects the central body 602 to the outer body 606. FIG. 4A shows a transverse section view of the fiducial 600 along line 4A-4A of FIG. 4.

FIG. 5 shows a bullet-shaped fiducial 700 with a central fiducial lumen 702 extending longitudinally through its body 701. A suture 710 extends through the fiducial lumen 702 and terminates distally in a T-anchor 712. The distal end of the fiducial body 701 is rounded, forming a distal bullet-like nose 704. The surface of the fiducial 700 includes a pair of domed protuberances 706.

Figure 6:
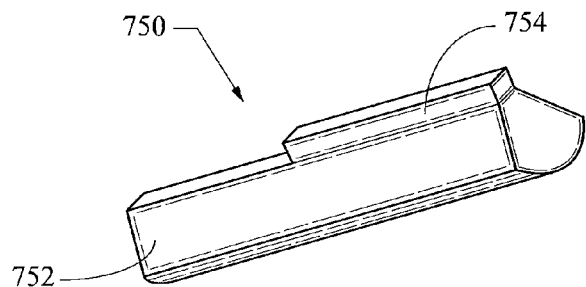
FIG. 6 shows a seventh fiducial embodiment.

The embodiments described above each include a body formed as a generally longitudinal central fiducial portion that is generally cylindrical. However, it should be appreciated that other fiducial embodiments may include a main body that is non-cylindrical, or that includes both cylindrical and non-cylindrical portions. FIG. 6 shows an embodiment of a non-cylindrical fiducial 750. The fiducial 750 includes a generally columnar body portion 752 with a generally round-based-triangular transverse cross section. It has a generally parallelepiped protuberance 754 along one surface. Its generally flat planar surfaces may provide a desirable echogenic profile, which may be enhanced by texturing (e.g., knurling, dimpling, ridging, or another feature) of the surface.

Figure 7:
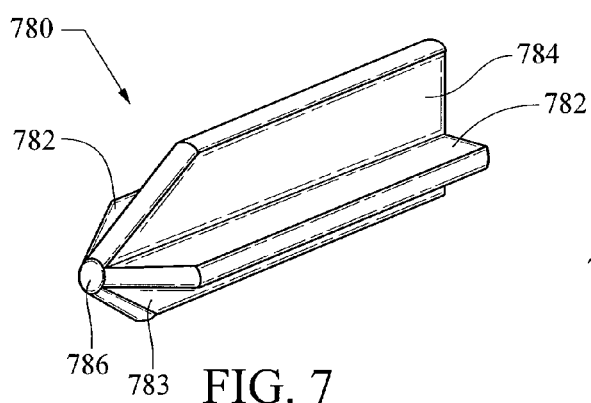
FIGS. 7-7A show, respectively, a top perspective view and a transverse section view of an eighth embodiment of a fiducial.
Figure 7A:
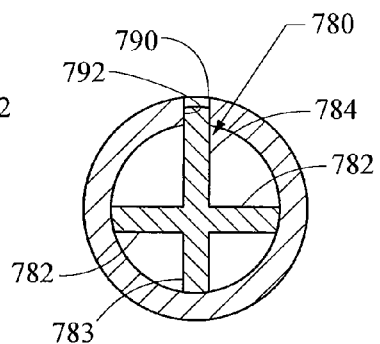

FIGS. 7 and 7A show another embodiment of a non-cylindrical fiducial 780. As is shown most clearly in the transverse section view of FIG. 7A, the fiducial 780 has a generally columnar body having a t-shaped cross-section with four protuberances. Two generally symmetrical protuberances 782 each have about the same dimensions—extending about the same distance from a central longitudinal axis, with a third protuberance 783 extending downward between them. The tip-edge of each preferably is at least slightly rounded to complement the outer curvature of a needle when placed therein. The fourth protuberance 784 preferably is taller (i.e., projects further from the central longitudinal axis) than the other three. The distal end 786 of the fiducial 780 is shown with a tapered geometry that may terminate in a sharp point or a rounded tip.

The transverse section view of FIG. 7A shows one way that the fiducial 780 may be used with a needle of the present system (e.g., with a needle 800 described below with reference to FIG. 8). The fiducial 780 is disposed slidably removably in the needle lumen. The fourth protuberance 784 extends into a needle slot embodied as a groove 792, and the difference between the height of the fourth protuberance 782 and the height of the symmetrical protuberances 782 (each measured from a center longitudinal axis of the fiducial 780) preferably is slightly less than the thickness of the wall of the cannula 790. The shorter protuberances preferably fit within the inner diameter of the needle lumen, and it is generally desirable that one or more of them contacts the needle lumen to keep the fiducial 780 aligned in the lumen, as well as to provide maximum surface area for desirable echogenicity. It should be appreciated that modified versions of this embodiment may be practiced within the scope of the present invention as defined by the claims. For example, it will be appreciated that two, three, or more protuberances may be used. Likewise, one or more of the protuberances may extend less than a full length of the fiducial and/or may be interrupted with one or more spaces along its length. The relative height of the protuberances may be varied along the length of various embodiments and/or within a single embodiment such that the heights of one or more protuberances are asymmetrical. Generally, it will be preferable for using this embodiment with a grooved needle that a groove-engaging protuberance extends further from a central longitudinal axis than all other protuberances.

Figure 8:
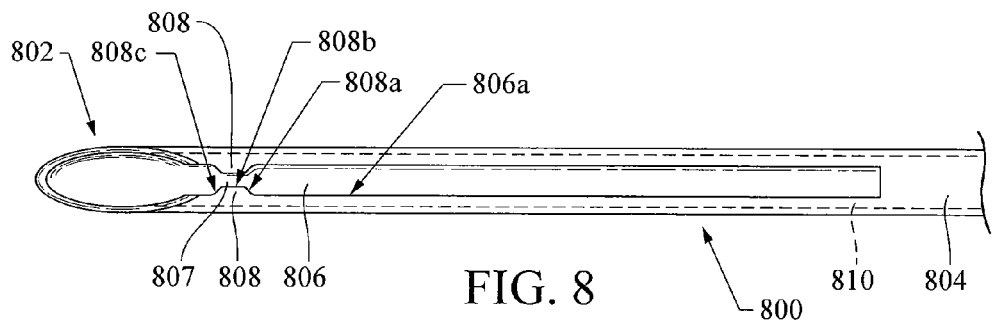
FIG. 8 shows a top view of a slotted needle embodiment.

FIG. 8 shows an embodiment of a fiducial introduction needle 800. The needle 800 is illustrated with a beveled distal tip 802. Its tubular cannula body 804 includes a longitudinal needle slot 806 along a distal end region of the cannula 804. The slot 806 preferably includes at least one detent including at least one detent surface, and more preferably two detents. The slot 806 is shown as being open through the entire wall of the cannula 804, but it should be appreciated that the slot may extend less than the thickness of the needle wall, such that it is embodied as a groove.

Figure 8A:
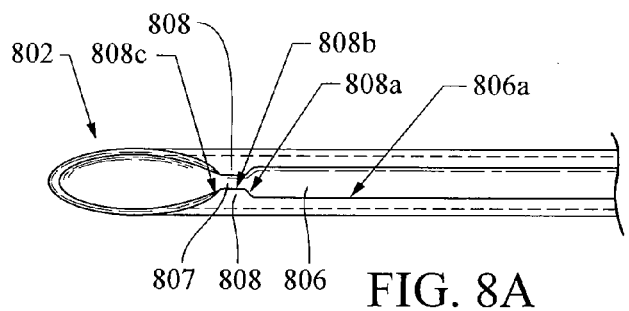
FIG. 8A shows a top view of another slotted needle embodiment.

In the embodiment of FIG. 8, the detent is formed as a narrowed portion 807 of the slot 806 between two tabs 808. The tabs 808 are generally trapezoidal, but may have a different geometry in other embodiments. As shown in FIG. 8A, in certain preferred embodiments, the tabs 808 may be located immediately adjacent the distal bevel (e.g., to maximize efficiency of advancing a fiducial past them and out of the needle while minimizing residual overlap of a deployed fiducial with the beveled portion of the distal needle tip). Each of the transitions between the edge 806a of the needle slot 806, the proximal tab edge 808a, central tab edge 808b, and distal tab edge 808c may be cornered (e.g., chamfered or filleted) or rounded (e.g., radiused). The tabs 808 preferably are near the distal end of the slot 806.

The body wall cannula 804 generally circumferentially defines a needle lumen 810 configured to allow sliding passage therethrough of a fiducial such as, for example, a fiducial (e.g., those shown in FIGS. 2A-2D or others that would readily pass through the needle lumen 810, preferably with controllable retention of the fiducial(s) by the tabs 808). The needle may be constructed from a nickel-titanium alloy, cobalt-chromium (CoCr) alloy, stainless steel or any other suitable material. Its tip may have a different geometry than the beveled configuration shown. In an alternative embodiment, the tabs 808 may meet such that they will be forced to flex upward and/or outward to a greater degree to allow passage of a protuberance on a fiducial. And, the outer surface of the needle may be dimpled or otherwise textured to provide enhanced echogenicity.

An exemplary needle embodiment is also described with reference to FIG. 8, which exemplary needle embodiment may be configured and dimensioned for use with the exemplary fiducial needle embodiment described above with reference to FIGS. 2C-2D. In one such exemplary needle embodiment, the ID of the needle lumen is at least about 0.034 inches (0.86 mm). The OD of the needle is about 0.042 inches (1.07 mm; about 19-gauge), with a wall-thickness of about 0.008 inches (0.2 mm). The slot portion proximal of the tabs is about 0.02 inches (0.5 mm) wide and about 0.42 inches (about 10.7 mm) long. Each of the tabs extends about 0.06 inches (0.15 mm) out of the slot edge and has a slot-facing edge that is about 0.02 inches (0.5 mm) long (not including the proximal and distal angled transitions from the slot edge, which are radiused at about 0.005 inches (0.13 mm)). These measurements and proportions may be varied in other embodiments, including those illustrated herein, while remaining within the scope of the presently-claimed material. For example, the particular dimensions of a slot, tabs, and fiducial may be configured for use with a 22-gauge needle having a desirable balance of flexibility and stiffness, as well as including a distal needle tip bevel of about 30°, a slot width of about 0.014 inches (about 0.36 mm) with slot tabs separated only by about 0.006 inches (about 0.15 mm) across the slot, and echogenicity-enhancing surface dimpling disposed along the needle exterior adjacent and generally parallel with at least a distal length of the slot.

Figure 9:
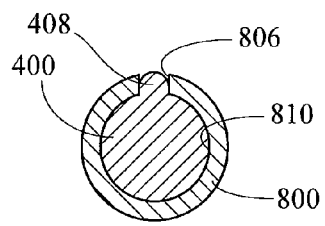
FIG. 9 shows a transverse section view of the needle of FIG. 8, with a fiducial disposed in its lumen.

FIG. 9 shows a transverse section end view of a section of a needle 800 (as in FIG. 8) and a fiducial 400 (as in FIGS. 2C-2D). This view shows the preferred close tolerances and a preferred orientation of the fiducial body relative to the needle lumen 810 and the protuberance 408 relative to the needle slot 806.

The distal end portion of a fiducial deployment system 1000 is described with reference to FIG. 10, which is an external view, and FIG. 10A which is a longitudinal section view taken along line 10A-10A of FIG. 10, using the needle 800 and fiducial 400 described above. The system 1000 includes a flexible elongate needle sheath 1002. The needle 800, including a more flexible proximal body portion 820 extends through a sheath lumen 1004. At least one fiducial 400, illustrated here as a plurality of fiducials 400, is disposed slidably removably in a distal region of the needle lumen 810 of the needle's cannular body. The central longitudinal body portion 402 substantially occupies the inner diameter of the needle lumen 810. The protuberance 408 of each fiducial 400 has a height that may be about the same as the thickness of the needle wall, including the slot 806 into which the protuberances 408 project.

The protuberance 408 of the distal-most fiducial 400 is captured against the tabs 808 of the needle 800. A stylet 1006 configured for use as a pusher is disposed through a portion of the needle lumen 810 and preferably is configured for actuation from the proximal end, whereby it can be used to distally advance/push out the fiducials and/or hold them in place as the needle is withdrawn from around them. The presence of the fiducials and stylet in the needle 800 preferably improve its columnar strength reduce the likelihood that it will get bent, crimped, or otherwise damaged as it is navigated through and out of the distal end of an endoscope working channel (not shown).

Several different handle embodiments may be used to effect advancement and release of one or more fiducials. Certain handle embodiments are described with reference to FIGS. 16A-19D below, including with reference to the structure and method described below with reference to FIGS. 10-10A and 11A-11C.

Figure 10:
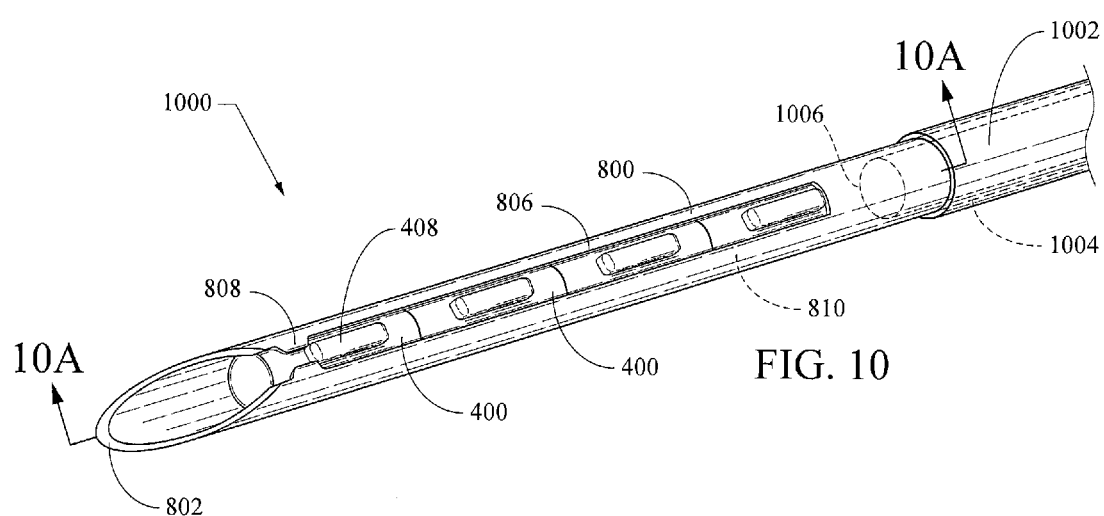
FIGS. 10-10 show, respectively, a top perspective view and a longitudinal section view of a fiducial deployment system.
Figure 10A:
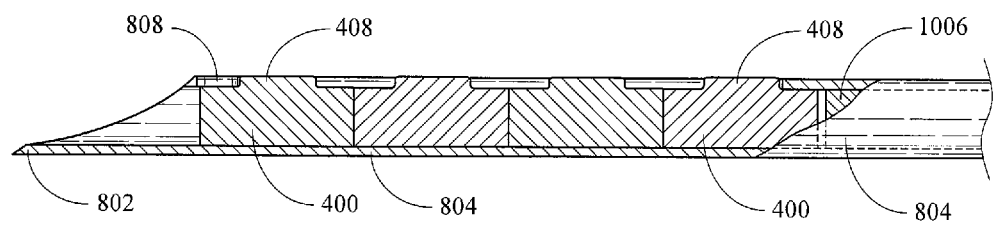

A method of using the fiducial deployment system of FIGS. 10-10A is described with reference to FIGS. 11A-11C, with reference to the structures shown in greater detail in FIGS. 10-10A. In a preferred method of use, an endoscope 1100 is provided, including a working channel 1102. In one preferred method, the endoscope is an EUS endoscope including a distal ultrasound array 1104 configured for ultrasound imaging. The endoscope 1100 preferably also includes a video element 1106 (e.g., CCD, optical camera, or other means for optical visualization). The methods below are described with reference to placing fiducials 400 at the margins of a tumor 1152 of a patient's pancreas 1150, such that the needle body will be of sufficient length and navigability (e.g., pushability and flexibility) to perorally be directed through a patient's gastrointestinal tract to a target site, including doing so via a working channel of an endoscope such as a gastric endoscope, colonoscope, anuscope, or other visualization/procedure-assisting device.

Figure 11A:
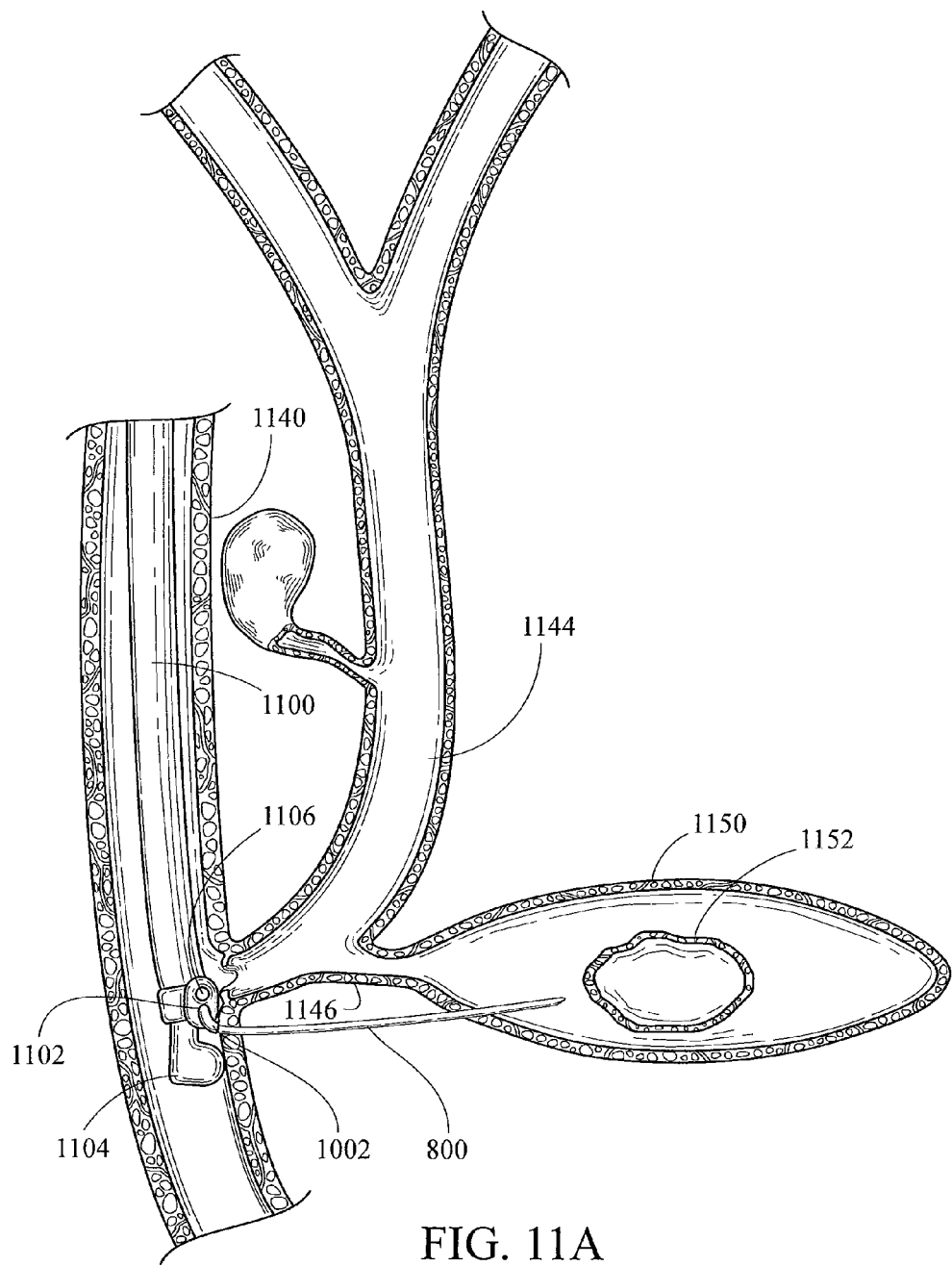
FIGS. 11A-11C show a method of placing fiducials.
Figure 11B:
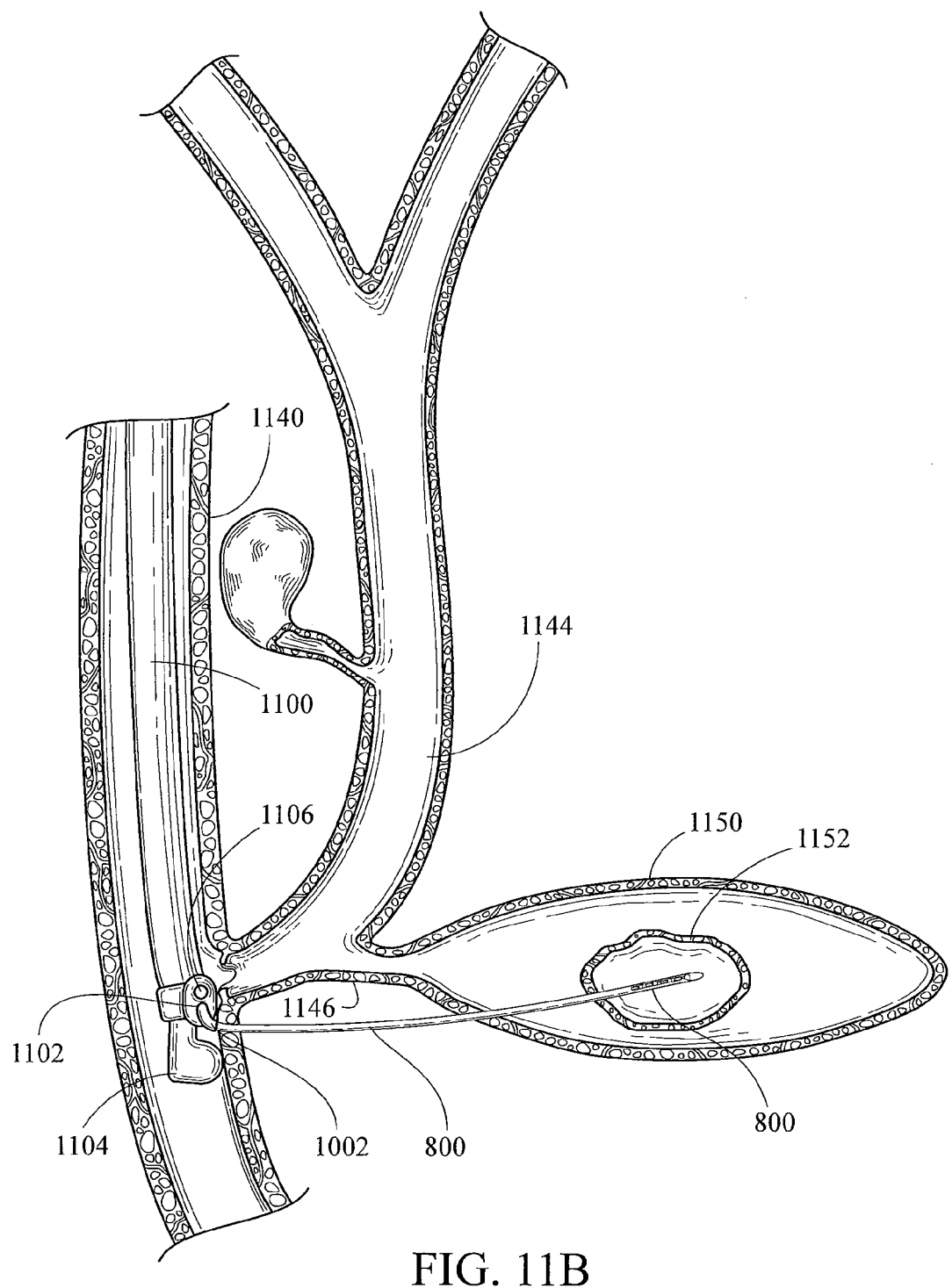
Figure 11C:
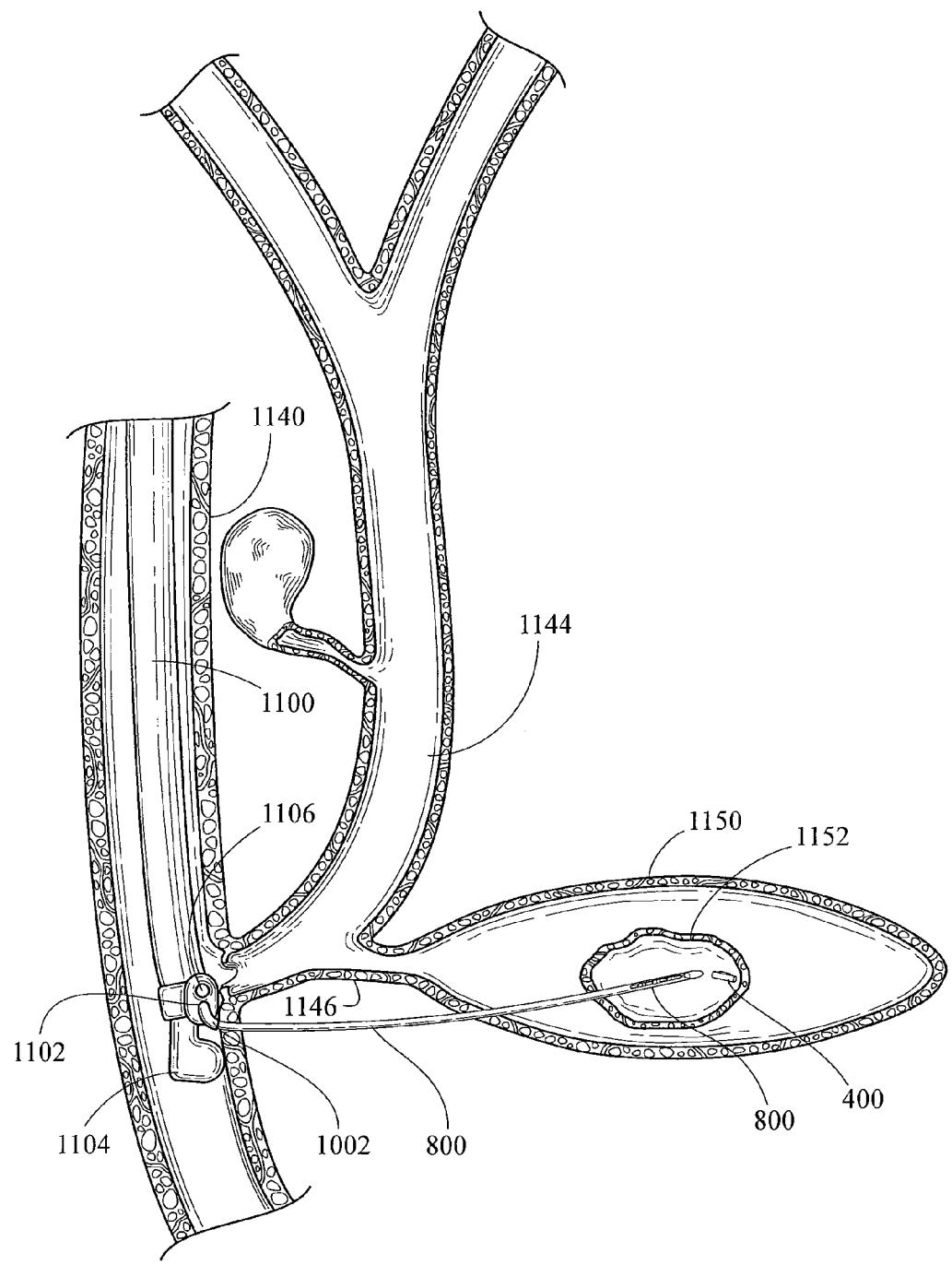

The endoscope 1100 is shown in FIG. 11A as having been directed through a patient's duodenum 1140 until its distal end portion is adjacent the Sphincter of Oddi 1142, which provides access to the common bile duct 1144 from which the pancreatic duct 1146 branches and leads to the pancreas 1150.

As shown in FIG. 11A, the sheath 1002 has been advanced to the duodenal wall and the needle 800 has been pierced therethrough, extending near the pancreatic duct 1146 to a location adjacent the tumor 1152 in the pancreas 1150. As shown in FIG. 11B, the needle 800 is directed to a first target site at a margin of the tumor 1152 (preferably under ultrasound guidance, which can be replaced, complemented, and/or verified by fluoroscopy or another visualization technique). Once the distal end 802 of the needle 800 is positioned at the first target, the distal-most fiducial 400 therein is deployed. In one aspect, the deployment may be accomplished by positioning the distal needle end 802 and the fiducial 400 therein at the first target, then retracting the needle 800 while retaining the position of the stylet 1006 such that the fiducial 400 remains in the desired first target position. In another aspect, the deployment may be accomplished by positioning the distal needle end 802 and the fiducial 400 therein adjacent the first target, then holding the needle 800 in position while advancing the stylet 1006 such that the fiducial 400 is advanced into the desired first target position.

As will be appreciated from the structure of the needle 800 and fiducials 400 as shown in FIGS. 10-10A, a user preferably will be able to control advancement/deployment of the fiducials to one at a time, such that a plurality of fiducials (without any spacers) may serially—but separately and independently—directed into different locations. Then the fiducial 400 is in a "ready to deploy" position, its distal protuberance face 408a is engaged against the proximal tab edges 808a. To deploy the fiducial 400, the user must move one of the stylet 1006 or needle 800 relative to the other with sufficient force to advance the protuberance 408 through the tabs 808.

The user preferably will have a tactile sense of resistance as the protuberance 408 passes through the tabs 808, which resistance will decrease immediately as soon as the protuberance clears the tabs. Then the user preferably continues the relative motion of stylet and needle until resistance is again encountered, indicating that the next fiducial behind the distal-most one has met the proximal tab edges 808a.

It will often be preferred that the fiducials (and the protuberances thereon) be proportioned such that complete deployment of a distal-most fiducial includes it substantially clearing the distal needle tip 802 and coincides with the protuberance of the next distal-most fiducial meeting the proximal tab edges 808a. As such, it may be advantageous in some fiducial embodiments to position the protuberance more proximally on the fiducial body such that a fiducial body portion distal of the protuberance is longer than a body portion proximal of the protuberance. (See, for example, the fiducial 200 in FIG. 2A; it should be appreciated that the protuberance of almost any fiducial embodiment in keeping with principles of the present invention may be disposed near the proximal end up to and including flush with the proximal end of the fiducial body). FIG. 11C shows the fiducial in place, with the needle withdrawn away from it.

Next, the user may retract the needle 800 into the sheath 1002 to a sufficient distance allowing it to be re-extended to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above.

Figure 11D:
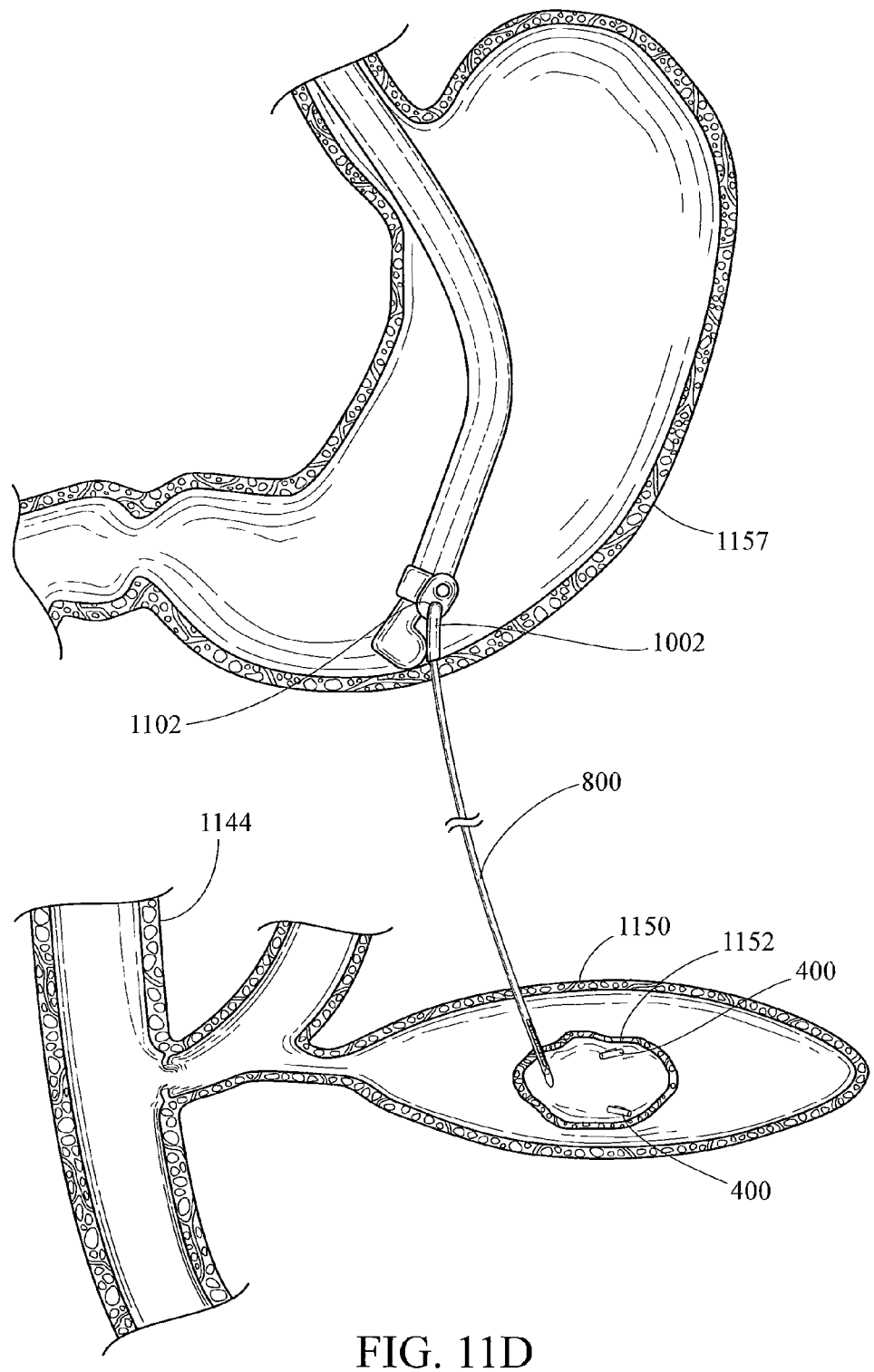

Preferred method embodiments are described with reference to FIGS. 11D and 11E, each of which will allow use of a larger needle and fiducials. The endoscope 1100 is shown in FIG. 11D as having been directed into a patient's stomach 1157. The sheath 1002 has been advanced until its distal end is adjacent the stomach wall, then the needle 800 has been advanced through the stomach wall, to the pancreas 1150, and into the tumor 1152. This stomach location is sufficiently near the target site (tumor 1152) to provide access to it for the fiducial introduction system. This method preferably is executed under ultrasound visualization using the ultrasound array 1104. Two other fiducials 400 are shown as having been placed in the tumor 1152 already.

Figure 11E:
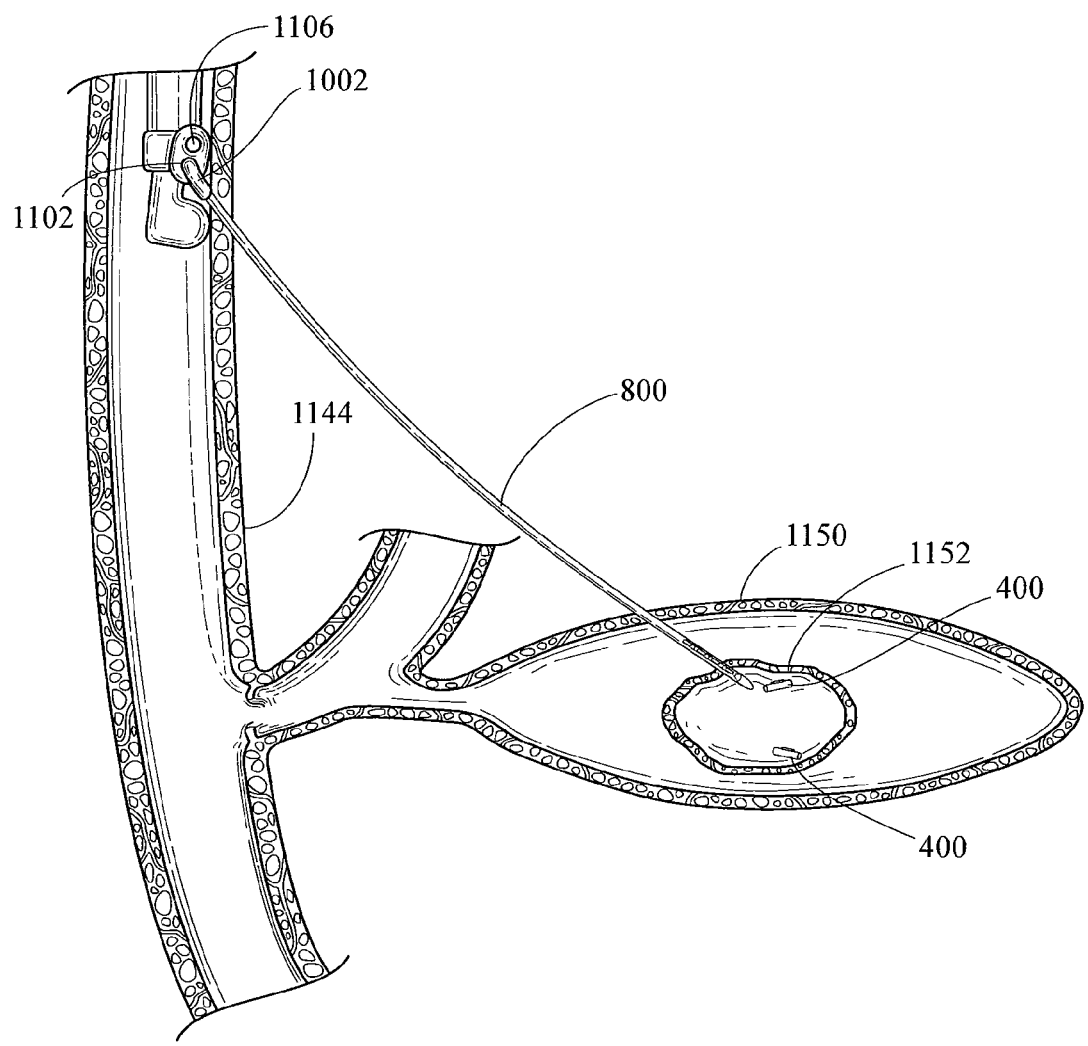

The endoscope 1100 is shown in FIG. 11E as already having been directed through a patient's duodenum 1140. The sheath 1002 has been advanced until its distal end is adjacent the duodenal wall, then the needle 800 has been advanced through the duodenal wall, to the pancreas 1150, and into the tumor 1152. This location in the duodenum 1140 is sufficiently near the target site (tumor 1152) to provide access to it for the fiducial introduction system. This method preferably is executed under ultrasound visualization using the ultrasound array 1104. One fiducial 400 is shown as having already been placed in the tumor 1152. The needle 800 has just released another fiducial 400 and has been partially retracted.

The ability to complete the method using direct/video and ultrasound imaging with little or no use of fluoroscopy presents an advantage of minimizing the radiation exposure of the patient (who may, for example, have to undergo radiation therapies where the total amount of exposure to radiation is desired to be minimized to that which is therapeutically and diagnostically necessary). Advantages of time and expense for the patient, physician and other treating/diagnostic personnel, and the treatment facility are likely as implementation of the present method may prevent all of those entities from having to schedule and conduct a second endoscopic procedure, and/or to extend the initial diagnostic procedure with the time-consuming methods and materials currently available in the prior art as described.

Figure 12A:
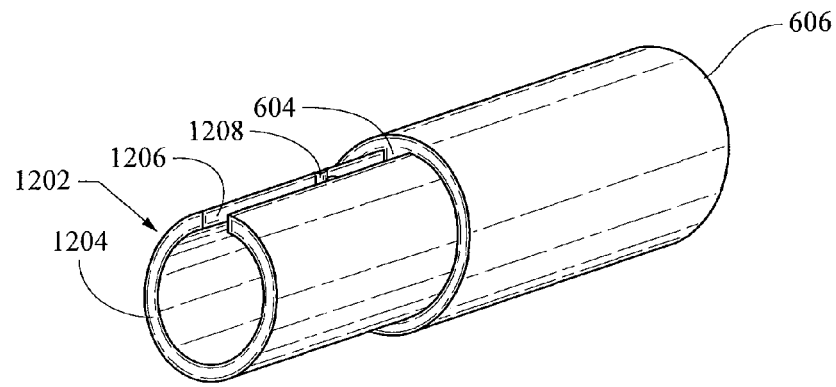
FIGS. 12A-12B show, respectively, top perspective and top plan views of another needle and fiducial embodiment.
Figure 12B:
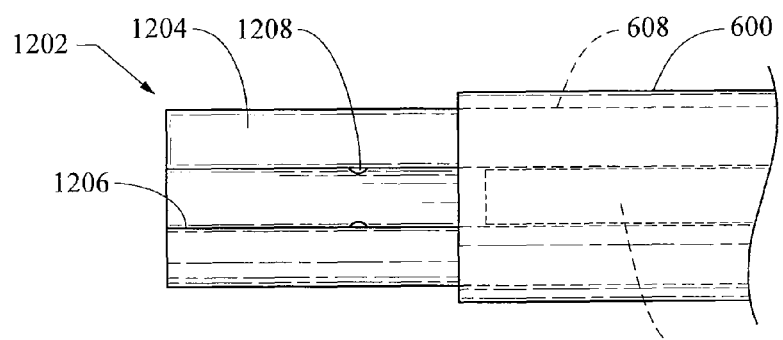

FIGS. 12A and 12B show a needle embodiment 1202 with the fiducial embodiment 600 discussed above with reference to FIGS. 4 and 4A. The needle 1202 includes a cannula body 1204 with a slot 1206 through the cannula body 1204. The fiducial 600 is mounted onto the needle 1202, which may be a smaller needle than is practical for use with fiducial embodiments such as those shown in FIGS. 2A-2E, 3, 5, 6, and 7, as the fiducial 600 includes a portion of its mass disposed around the outside of the needle. The needle cannula body 1204 is disposed through the fiducial needle lumen 608. The fiducial protuberance 604 extends through the needle slot 1206, providing for travel and controlled release as is described above. FIG. 12B shows a top view of the needle 1202, with its slot 1206, and a pair of small detent bumps 1208 on the distal slot edge.

Figure 13:
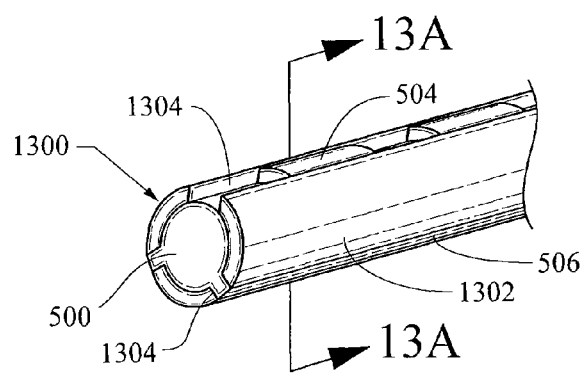
FIGS. 13-13A show, respectively, top perspective and transverse section views of another needle and fiducial embodiment.
Figure 13A:
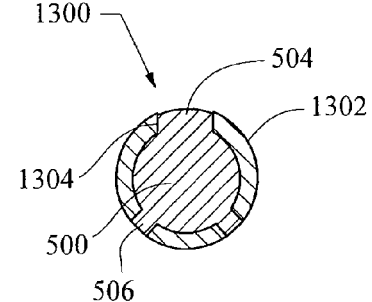

FIG. 13 shows a multi-slot needle 1300 such as might be useful with the fiducial embodiment 500 shown in FIG. 3. The needle 1300 includes a cannular body 1302 with three elongate slots 1304 extending along a distal length. Protuberances such as those (504, 506) shown in FIG. 3 can travel through the slots 1304. Two, three, or more than three slots may be present in other needle embodiments. FIG. 13A shows another view of the needle 1300, including a transverse section view along plane 13A-13A of FIG. 13, which view more clearly illustrates the interaction of the protuberances 504, 506 with the needle slots 1304.

Figure 14:
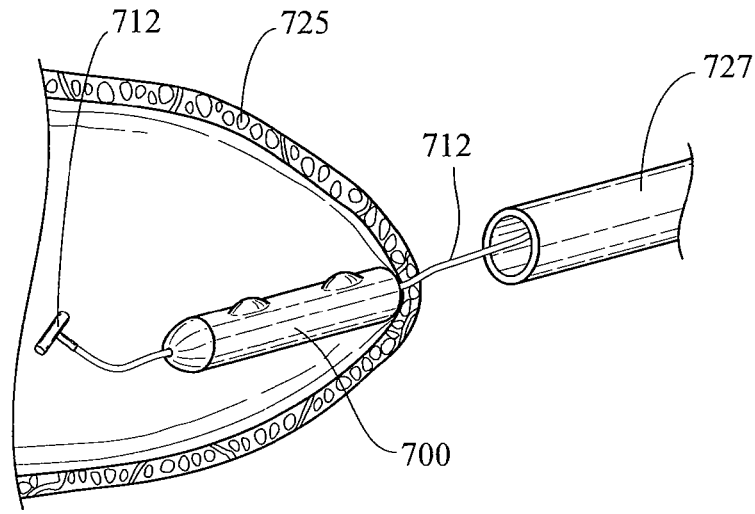
FIG. 14 shows a fiducial-placement method using a t-anchored suture.

FIG. 14 shows placement of a suture-mounted fiducial 700 of the type described above with reference to FIG. 5. In this illustration, a T-anchor-dispensing needle (not shown; these needles are well-known in the art) has been used to deposit a T-anchor 712 into target tissue 725, and the needle withdrawn. A fiducial 700 has been mounted onto the suture 710 and advanced with a pusher catheter 727 into the tissue 725. This structure and method provides a different means for placing a plurality of fiducials, which may or may not include protuberances (which, if present, may allow use of the fiducial 700 with a slotted needle in method operating generally as described above with reference to FIGS. 11A-11C).

Figure 15:
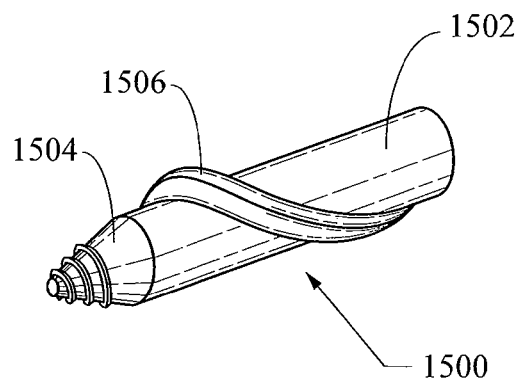
FIGS. 15-15A show, respectively, another fiducial embodiment and another needle embodiment configured for use therewith.
Figure 15A:
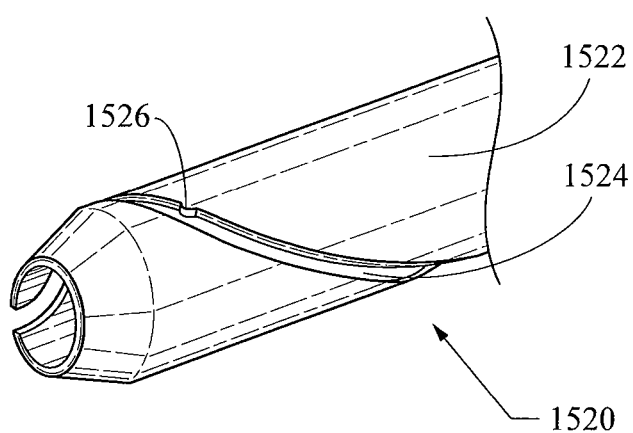

FIGS. 15A and 15B show, respectively, a rifling fiducial 1500 and slotted needle 1520 configured for use with it. The fiducial 1500 includes a generally cylindrical main body 1502 with a conical distal tip 1504 that may include a surface having a helically threaded texture. A protuberance 1506 is partially helically wrapped around the outer circumference of the body 1502. The needle 1520 for this fiducial 1500 is shown in FIG. 15B. It has a generally tubular cannula body 1522 with a helical slot 1524 configured to accommodate the protuberance 1506. The slot 1524 includes a single detent tab 1526 along one edge. As will be appreciated, a fiducial 1500 being advanced through the needle 1520 will riflingly rotate as it exits the needle. This rotation may help it advance more easily in certain tissue types.

Fiducials with generally cylindrical or otherwise generally regular geometry may migrate after having been placed in a desired location, including that—over the course of multiple treatments of a target area delineated by fiducials—they may migrate with changes in the condition of surrounding tissues. For circumstances where it may be advantageous to minimize migration, a fiducial may be used that includes one or more anchoring projections. FIGS. 20A-20F show several such embodiments.

Figure 20A:
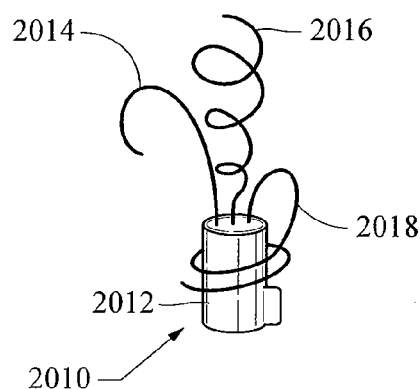
FIGS. 20A-20F show other fiducial embodiments.

FIG. 20A shows a fiducial 2010 including a generally cylindrical primary body 2012 that may be solid or partially hollow (and that may be treated to promote echogenicity). Three anchoring projections embodied as prongs 2014, 2016, 2018 extend from one end of the fiducial body 2012. The prongs 2014 may be formed of a memory metal material configured to be readily passable through a small needle lumen for introduction and then to assume the shape illustrated upon being released therefrom when the fiducial 2010 is deployed. It should be appreciated that only one (or two, three, or more) such prong(s) may be provided and that the prong shapes may be varied from those illustrated in these examples, all within the scope of the present invention. Prong 2014 is curved in a fish-hook shape, prong 2016 is formed as an expanding helical coil extending away from the body 2012, and prong 2018 is formed as a coil back towards and partially around the body 2012.

Figure 20B:
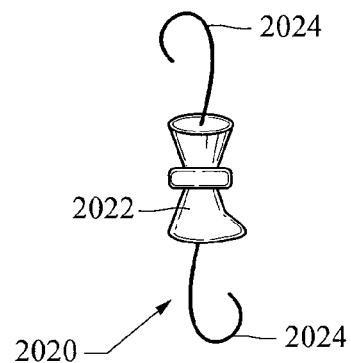
Figure 20C:
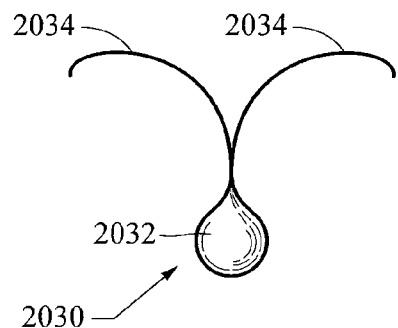
Figure 20D:
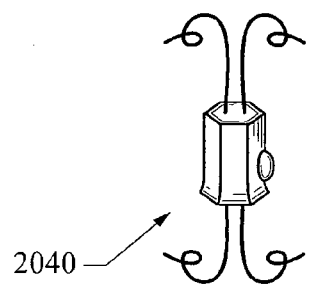
Figure 20E:
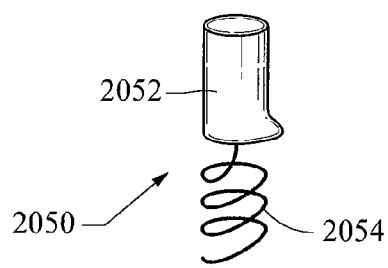
Figure 20F:
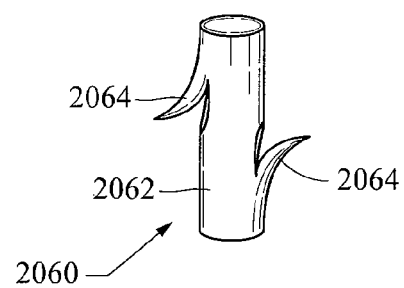

FIG. 20B shows a fiducial embodiment 2020 with two hooked prongs 2024 extending from opposite ends of a fiducial body 2022. FIG. 20C shows a fiducial embodiment 2030 with a tear-drop-shaped fiducial body 2032 with two widely-splaying prongs 2034. FIG. 20D shows a four-pronged fiducial 2040. FIG. 20E shows a single-pronged fiducial 2050 including a trailing coiled prong 2054 that may help to deploy the fiducial body 2052 beyond a needle bevel by pushing against a more proximal fiducial during deployment, then coiling to embed into adjacent tissue. FIG. 20F shows a barbed fiducial embodiment 2060. Anchoring projections, embodied as barbs 2064, may help to anchor the fiducial 2060 in tissue and may also function as part of the tracking/detent/release system described herein with reference to slotted needles. Specifically, one or both barbs 2064 may be configured to ride through a slot of a slotted needle and engage a fiducial-retention detent (e.g., one or both barbs 2064 may function similar to the fiducial protuberance 408, including interaction with the fiducial-retention detent embodied as tabs 808 of the needle 800 described above with reference to FIGS. 8-10A).

Figure 21:
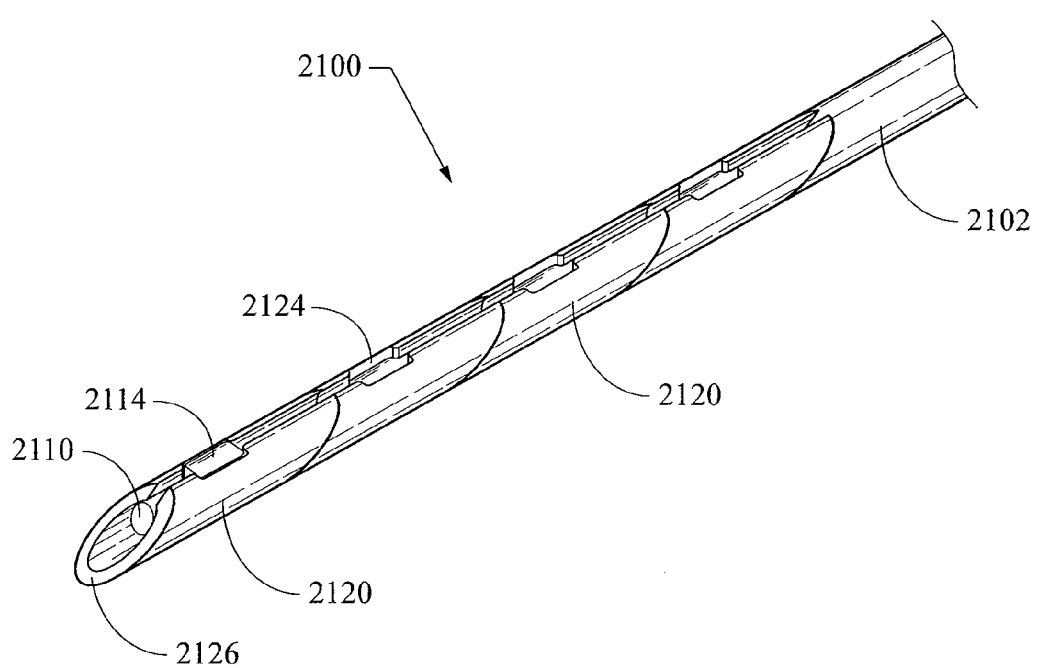
FIG. 21 shows the distal end of another fiducial deployment system embodiment, including one or more fiducials configured with a needle-like distal tip.

FIG. 21 shows another embodiment of a fiducial deployment system 2100. The system includes a plurality of fiducials 2120, each having a central lumen 2122 through which is disposed an elongate stylet 2110. The stylet 2110 extends lengthwise through a lumen of a needle cannula 2102. Each of the fiducials 2120 includes a fiducial detent surface 2124 configured to engage a complementary stylet detent surface 2114. In the pictured embodiment, the fiducial detent surface 2124 is configured as a pair of lateral indentations 2124, which will engage a stylet detent projection 2114 when its fiducial is in the distal-most position (although, in an alternative embodiment, more than one stylet detent surface may be provided to engage more than one fiducial). At least the leading fiducial 2120 preferably includes a beveled, pointed, or other traumatic/penetrating distal end, shown here as beveled fiducial tip 2126, such that the fiducial(s) will function(s) as a penetrating needle tip during advancement of the fiducials into target tissue (and the stylet 2110 may be provided with a complementarily beveled distal end to form a beveled needle-like distal end as each fiducial is engaged with the stylet detent 2114). It will be appreciated from FIG. 21 how a user may advance the cannula 2102, stylet 2110, and fiducials 2120 overlying the stylet into tissue, in a manner where the cannula forms a "needle base" that is completed/extended by the fiducials and stylet. The distal-most fiducial may be directed to a first target location, and advanced past the stylet detent projection 2114 (e.g., by retracting the stylet and/or advancing the cannula), whereupon a second fiducial then forms the tip of a needle-functioning structure that can be directed to a second location for deployment of another fiducial, repeating as desired.

Figure 16A:
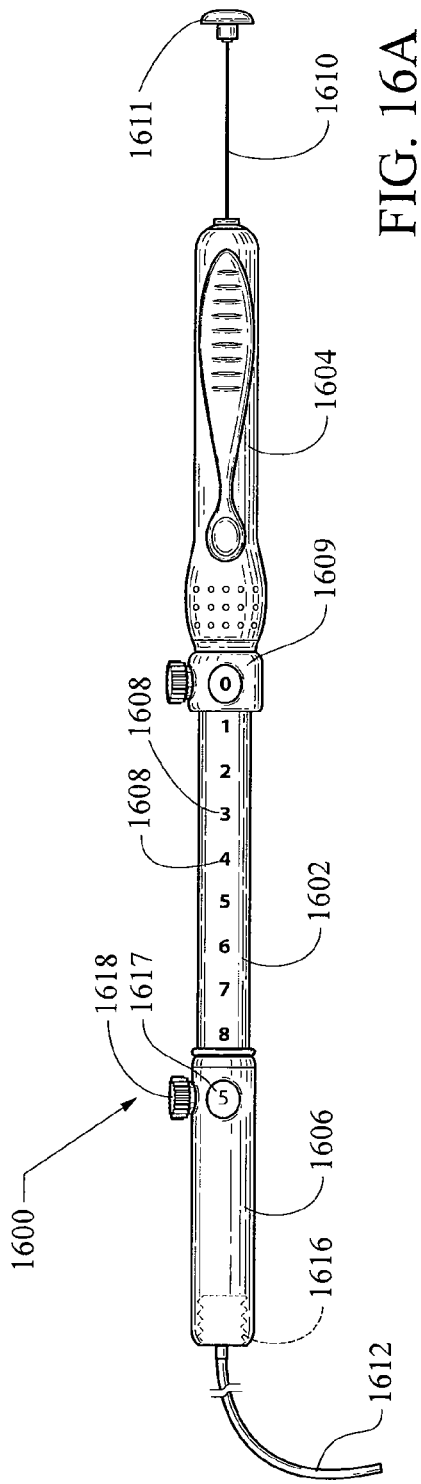
FIGS. 16A-16B show a handle embodiment for a fiducial deployment system.
Figure 16B:
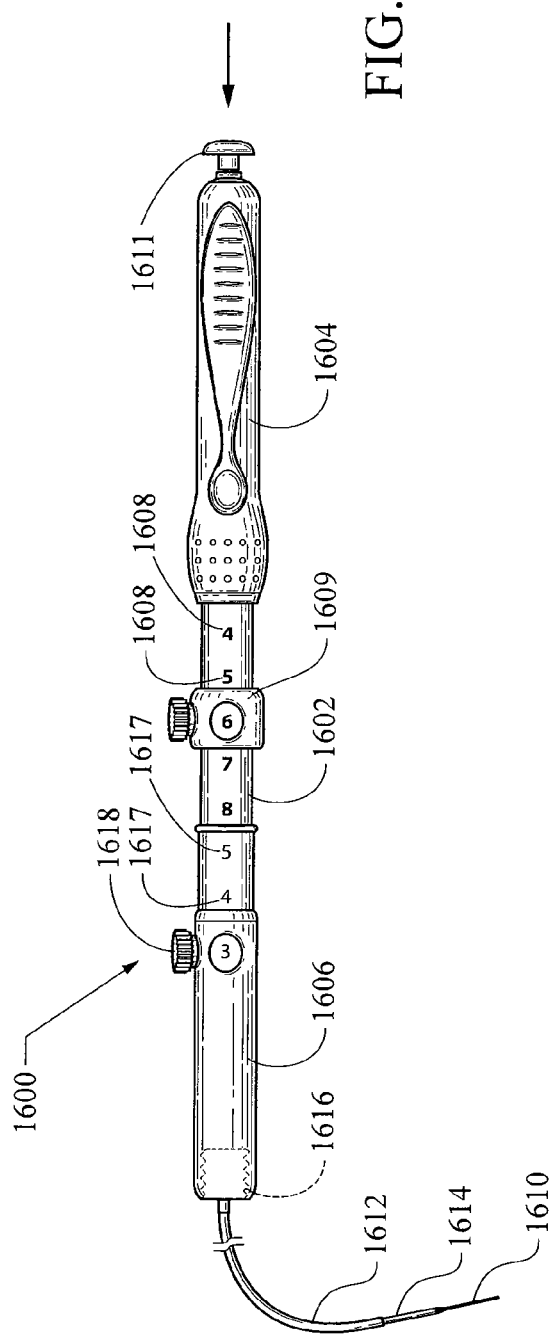

FIGS. 16A-16B show a handle embodiment 1600 that may be used with a fiducial deployment system. The handle 1600 includes a sheath-attached handle member 1602 with a needle-attached handle member 1604 longitudinally slidably disposed on its proximal end. A scope-attachment handle member 1606 is slidably attached to the distal end of the sheath-attached handle member 1602. The sheath-attached handle member 1602 is attached to the needle sheath 1612 and the needle-attached handle member 1604 is attached to the needle 1614 (which may be configured in the manner of any of the needles disclosed herein or later developed in accordance with principles of the present disclosure). The scope-attachment handle member 1606 is configured for incrementally fixable, longitudinally-adjustable (relative to the other handle components) attachment to the exterior of an endoscope working channel (not shown) using, for example, a threaded cavity 1616. The scope-attachment handle member 1606 allows a user to determine the distance by which the sheath 1612 will extend from a standard-length endoscope, and it may include numerical indicia 1617 corresponding to that relative length and an adjustable engagement structure 1618 allowing a user to select a length and engage the scope-attachment handle member 1606 accordingly. It should be appreciated that embodiments of the handle described and claimed herein may be practiced within the scope of the present invention without including a scope-attachment member.

The sheath-attached handle member 1602 includes numerical indicia 1608 and an adjustable ring 1609 that limits the movement of the needle-attached handle member 1604 and provides a way to select the distance to which the needle 1614 may be extended beyond the sheath 1612. By way of illustration, the configuration shown in FIG. 16A would allow the sheath to extend 5 units (e.g., inches, cm) beyond the distal end opening of an endoscope working channel, and the needle 1614 would not extend at all beyond the distal end of the sheath 1612. The configuration shown in FIG. 16A would allow the sheath to extend 3 units (e.g., inches, cm) beyond the distal end opening of an endoscope working channel, and the needle 1614 would be allowed to extend up to 6 units beyond the distal end of the sheath 1612, although its current position would be only about 4 units beyond the distal end of the sheath 1612.

A stylet 1610 extends through a lumen of the needle 1614 and has a stylet cap 1611 fixed on its proximal end. The stylet 1610 is shown as being retracted proximally in FIG. 16A, and extended beyond the distal end of the needle 1614 in FIG. 16B. The stylet 1610 may be manually advanced distally through the needle lumen in the same manner as described above (with reference to FIGS. 10-10A) for a stylet 1006. As such, a user may use the stylet to manually push fiducials out of a distal end of the needle 1614. If this method is used (e.g., in the manner described above for deployment of fiducials with reference to FIGS. 10-10A and 11-11E), a user must rely upon tactile feedback to determine when a fiducial has been advanced beyond any detents, which may be difficult through a long stylet—particularly if the detents are rounded such that the advancing motion is relatively smooth. Accordingly, it may be advantageous to provide an advancement mechanism configured to attach to (including being integrated with) the handle 1600 that provides improved control of stylet advancement.

Figure 17B:
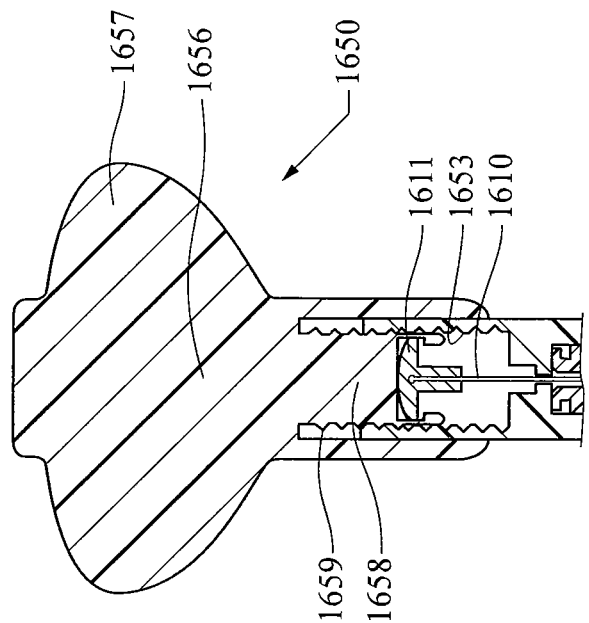
FIGS. 17A-17B show an advancement mechanism embodiment for a handle of a fiducial deployment system.

FIGS. 17A-17D show an advancement mechanism assembly 1650 for the handle 1600. The advancement mechanism includes an anchor member 1652 configured to attach to (or be integrated with) the needle-attached handle member 1604. This attachment configuration will provide for control of stylet-advancement relative to the needle 1614, in a manner configured to allow execution of the fiducial deployment method described with reference to FIGS. 11A-11E (e.g., by advancing the stylet and/or retracting the needle by predetermined lengthwise increments). This advancement mechanism embodiment includes a threaded rotatable advancement member 1656, which includes wings 1657 to provide mechanical advantage/leverage during rotation (as well as potentially serving as clear visual indicia of degree of rotation). As shown in the longitudinal section view of FIG. 17B, the rotatable advancement member 1656 includes an extension 1658 with an external threaded surface 1659 configured to engage an internal threaded surface 1653 of the anchor member 1652. The extension 1658 also engages the stylet cap 1611. As shown in FIG. 17B (which is a longitudinal section view taken along the plane of the wings 1657), rotating the rotatable advancement member 1656 will advance it and the stylet 1610 distally relative to the anchor member 1658, needle-attached handle member 1604, and needle 1614. Those of skill in the art will appreciate that the handle 1600 with assembly 1650 may be used to deploy one or more fiducials in the same manner as shown in FIGS. 11A-11E.

Figure 17A:
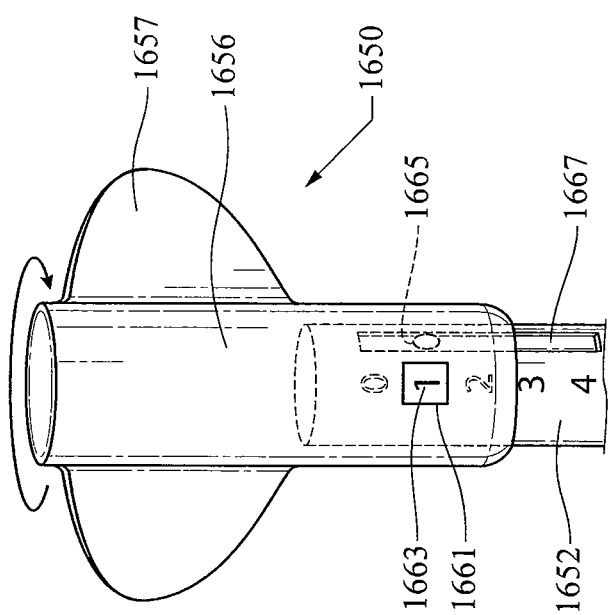

FIG. 17A also shows indicia features that may enhance a user's experience with the assembly 1650. The pitch and size of the threads in the threaded surfaces 1653, 1659 may be calibrated such that a predetermined degree of rotation will advance the advancement member 1656 and stylet 1610 by a predetermined longitudinal distance that corresponds to (i.e., is the same as, or has a specific correlational relationship to) advancement and/or deployment of a fiducial disposed in the distal needle lumen. Examples of visual, auditory, and tactile indicia are provided and may be used alone or in any combination in the form depicted here or in any other form known or developed in the art—all within the scope of the present invention. The assembly 1650 is depicted as being configured such that one full rotation of the rotatable member 1656 will advance the rotatable member 1656 and stylet 1610 a longitudinal distance sufficient to deploy one fiducial (see, e.g., FIG. 11C). Accordingly, one visual index of advancement is a user's degree of rotation of the rotatable member.

In certain embodiments, it may be preferable to configure the pitch and size of the threads or other advancement means such that only a minimal degree or increment of rotation is required to advance the stylet and/or retract the needle a predetermined distance (that may be an absolute distance or a relative distance of movement between the needle and stylet) sufficient to deploy a fiducial. For example, it may often be helpful to provide for one-handed actuation of the advancement member 1656 by a user being able to grasp the needle-attached handle member 1604 in his/her palm and actuate/rotate the advancement member 1656 with his/her thumb sufficiently to advance a fiducial without significantly altering the grip, and—preferably—without necessitating awkward movements or significant repositioning of either of the user's hands. It will be appreciated that the size, shape, and location of the wings 1657 or equivalent structures (e.g., protruding structures, textured surfaces, or other means for actuating the advancement member) may be located and oriented in a manner that would be easily accessed and actuated by a thumb and/or finger combination of a user without awkward positioning or repositioning of the user's hand.

One visual index shown is an aperture 1661 showing a numeral 1663 indicating the number of fiducials that have been deployed (in FIG. 17A, one fiducial is indicated as having been deployed). Tactile and auditory indicia are also provided in the form of a detent bump 1665 on an interior surface of the rotatable member 1656 and a groove 1667 on an exterior surface of the anchor member 1658. As shown in FIG. 17A, the bump 1665 engages the groove 1667 when the rotatable member 1656 is in a neutral/non-deploying position. The bump 1665 disengages from the groove 1667 as the rotatable member 1656 is turned, and then will re-engage with a "click" that may be heard and felt by the user when one full rotation has been executed. It should be appreciated that, in other embodiments where the pitch and site of the threads have been configured differently, or where there is a different (e.g., non-threaded) advancement means employed, more than one detents and/or grooves may be used to indicate incremental advancement corresponding to a predetermined full or partial deployment of a fiducial (e.g., in an embodiment where a 90-degree rotation is sufficient to advance the stylet longitudinally a distance that deploys a fiducial from the distal needle end). Those of skill will also appreciate that other indicia for counting fiducial deployment and/or otherwise measuring advancement of the stylet and rotation of the rotatable member may be employed within the scope of the present invention.

Figure 17C:
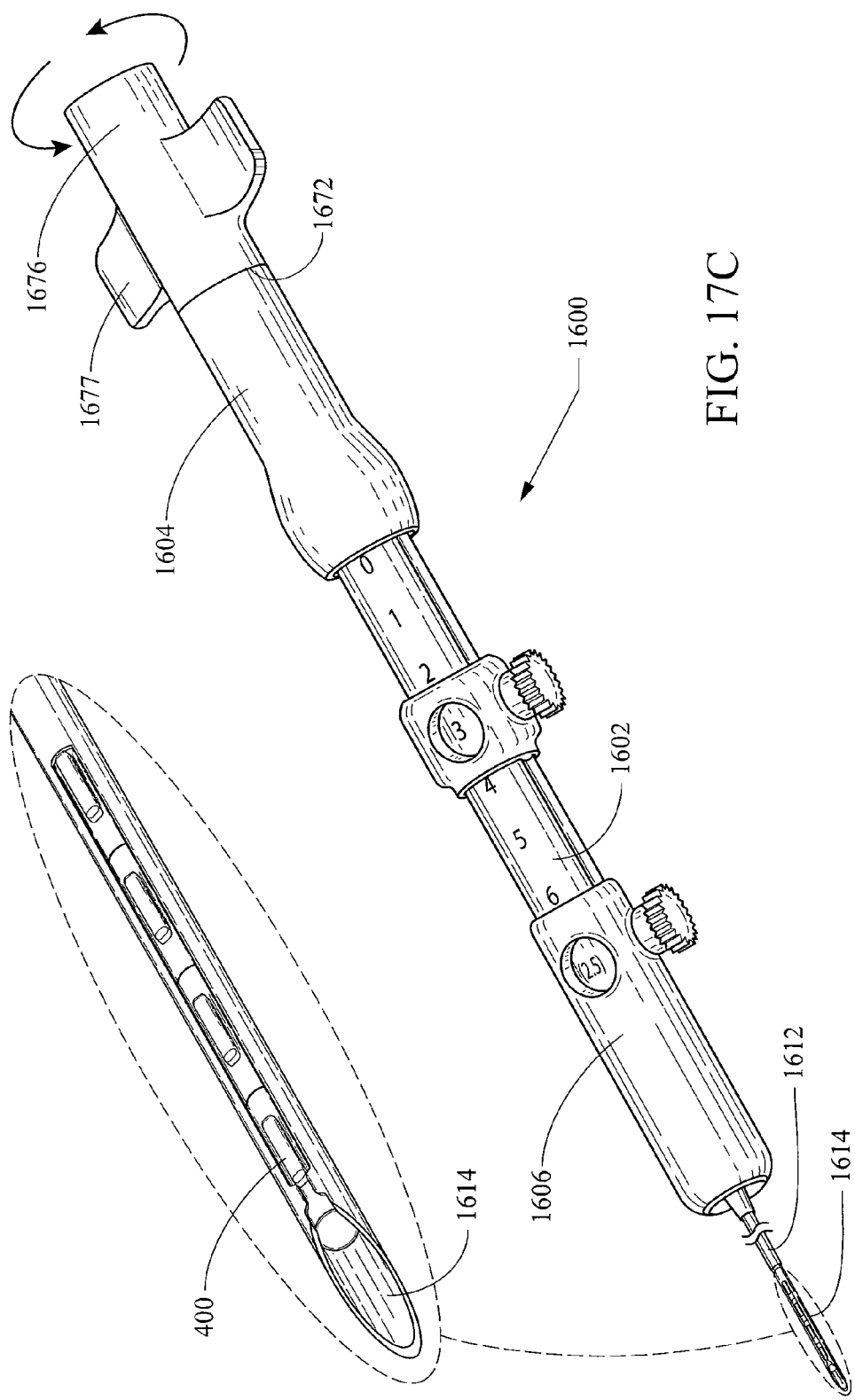
FIGS. 17C-17D show an advancement mechanism embodiment for a handle of a fiducial deployment system modified from that shown in FIGS. 17A-17B.
Figure 17D:
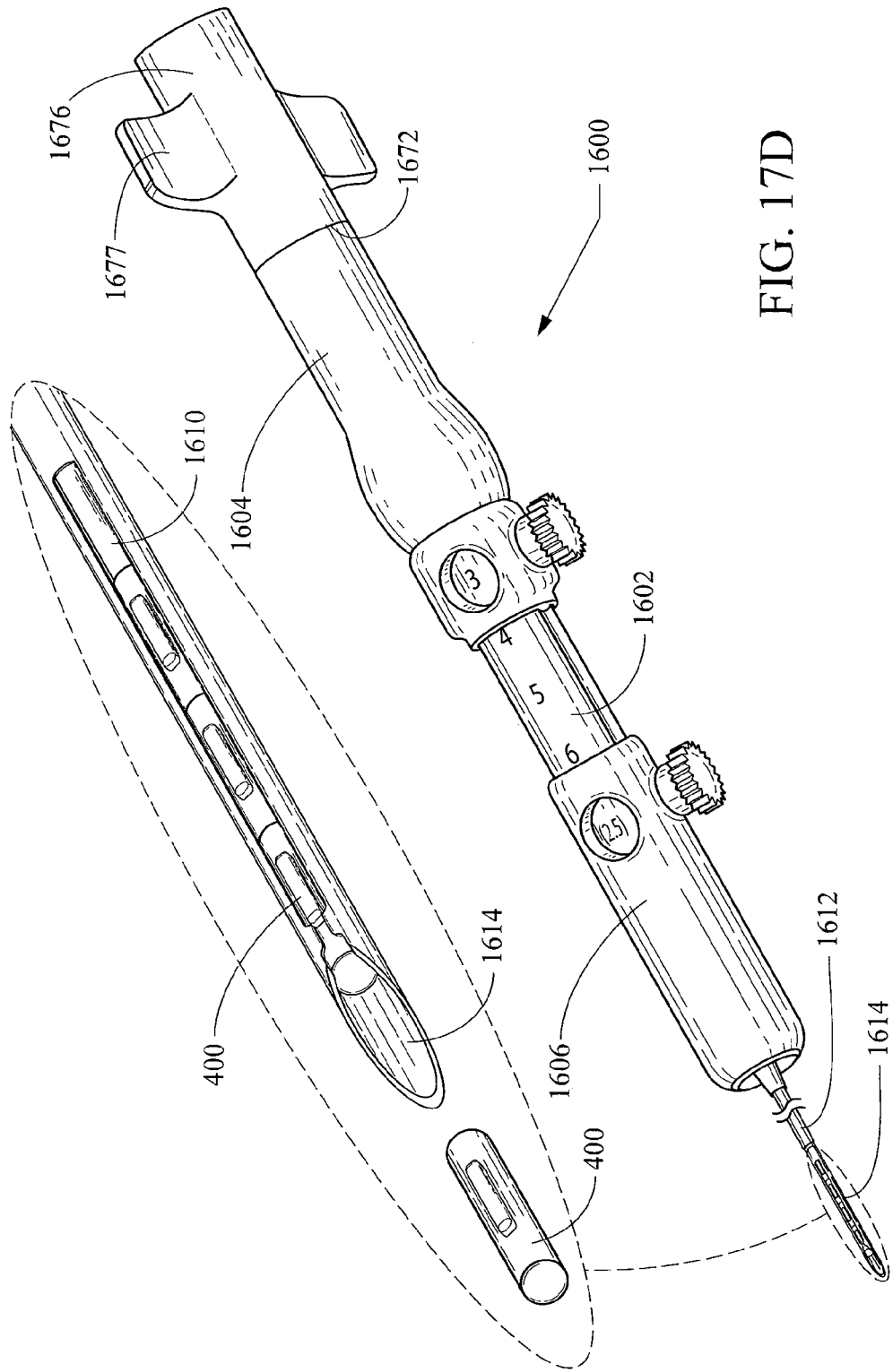

FIGS. 17C-17D show a fiducial deployment system with a handle 1600 having an advancement mechanism assembly 1670 (where like reference numbers are used to correspond with the advancement mechanism assembly 1650). The needle 1614 is advanced distally of the sheath 1612. An anchor member 1672 is attached by integration with the needle-attached handle member 1604 (or, the anchor member may be formed by an integral proximal portion of the needle-attached handle member 1604). This attachment configuration will provide for control of stylet-advancement relative to the needle 1614 and fiducials 400, which are shown in greater detail in the magnified inset portion of each of FIGS. 17C and 17D. The advancement mechanism also includes a threaded rotatable advancement member 1676, which includes wings 1677 to provide mechanical advantage/leverage during rotation (as well as potentially serving as visual indicia of degree of rotation). The rotatable advancement member 1676 may include a threaded surface configured to matingly engage a complementary threaded surface of the anchor member 1672. The threaded rotatable advancement member 1676 also engages the stylet 1610 (although that engagement is not visible in the figures).

As shown in FIG. 17D, rotating the rotatable advancement member 1676 by a quarter-turn will advance it and the stylet 1610 distally relative to the anchor member 1672, needle-attached handle member 1604, and needle 1614. Those of skill in the art will appreciate that the handle 1600 with assembly 1670 may be used to deploy one or more fiducials in the same manner as shown in FIGS. 11A-11E. The magnified detail of the FIG. 17D inset shows how the stylet 1610 has been advanced to deploy/eject a fiducial 400.

Figures 18A, 18B:
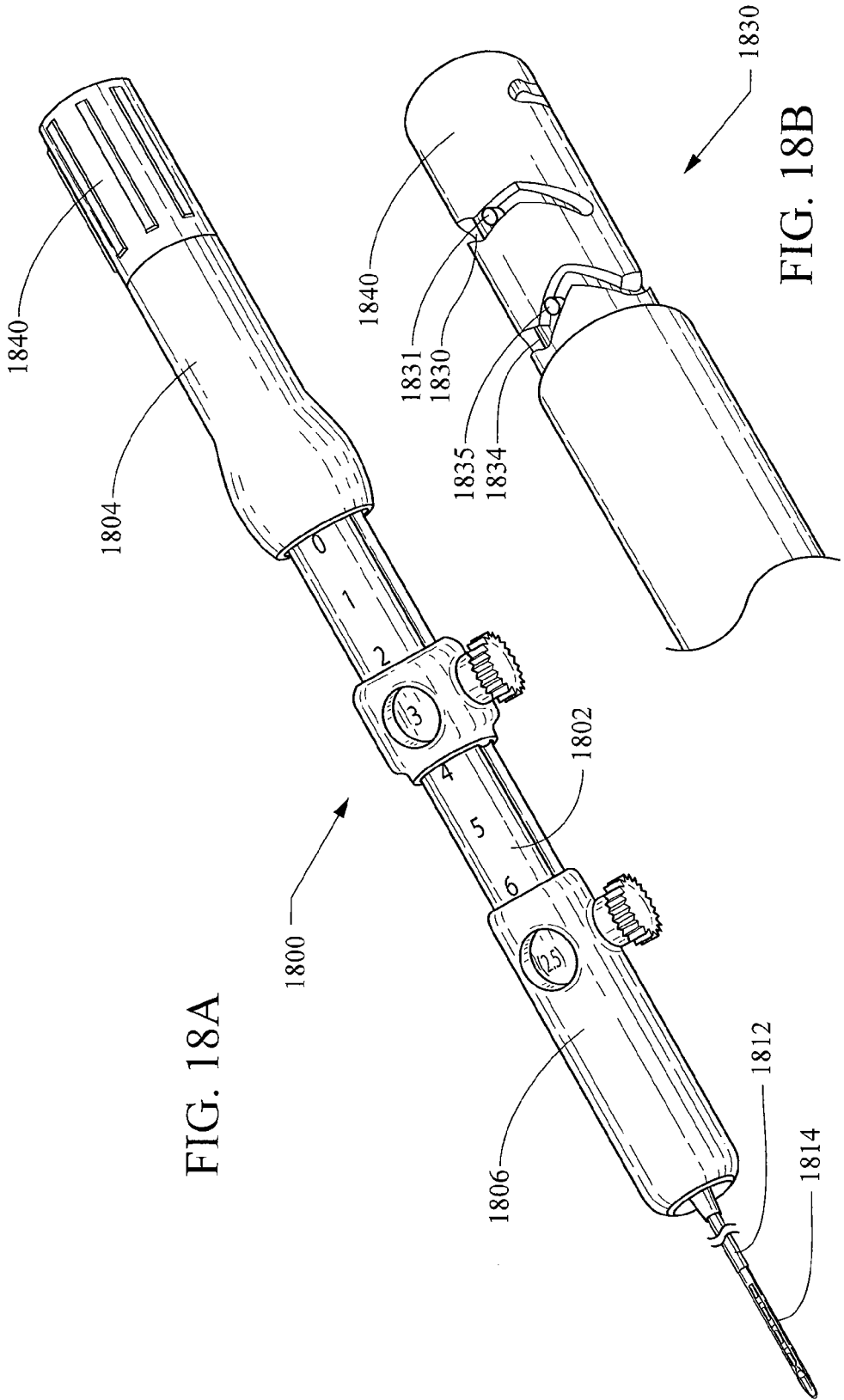

FIGS. 18A-18D show another handle embodiment 1800, using a rotational incremental advancement mechanism. As shown in FIG. 18A, the handle 1800 includes a sheath-attached handle member 1802 with a needle-attached handle member 1804 longitudinally slidably disposed on its proximal end. A scope-attachment handle member 1806 is slidably attached to the distal end of the sheath-attached handle member 1802. The sheath-attached handle member 1802 is attached to the needle sheath 1812 and the needle-attached handle member 1804 is attached to the needle 1814 (which may be configured in the manner of any of the needles disclosed herein or later developed in accordance with principles of the present disclosure). A stylet 1810 (shown in FIG. 18C) extends through the needle lumen.

FIGS. 18B and 18D show details of an advancement mechanism assembly 1830 for the handle 1800. The advancement mechanism includes an internally-tracked deployment handle member 1840 rotatably connected to the needle-attached handle member 1804. This attachment configuration will provide for control of stylet-advancement relative to the needle 1814 and needle retraction relative to the stylet 1810, in a manner configured to allow execution of a fiducial deployment method. FIG. 18B shows the internal dual track of the rotatable handle 1840 (as if the outer layer of the handle 1840 were removed to expose the tracks on its inward-facing surface). The dual track includes a needle-boss track 1834 and a stylet-boss track 1830, each of which form a zig-zag-like pattern effectively functioning as detent stops. A needle boss 1835 is attached to the needle 1814 and configured to move it longitudinally. A stylet boss 1831 is attached to the stylet 1810 and configured to move it longitudinally. The tracks are not continuously parallel, but rather are patterned to provide for controlled differential movement configured for deployment of one or more fiducials by a combination of stylet-advancement and needle-retraction. And, the interaction of the bosses with the tracks functions as (and may have its structure altered in a variety of ways to serve as) a detent-detent interface. This embodiment may include visual indicia, tactile indicia, audible indicia, or a combination thereof, and wherein said indicia is configured to correspond to a known longitudinal movement distance of the stylet, including as described above with reference to FIG. 17A. It should also be appreciated that one of skill in the art may—in view of the present disclosure, and within the scope of the present invention—readily alter the pattern of the tracks shown here for illustrative purposes in order to provide a different pattern of advancing and/or retracting the stylet and needle relative to each other.

FIG. 18D diagrammatically shows the tracks 1830, 1834 laid out as if the inner tracked surface of the rotatable handle 1840 had been "unrolled." FIG. 18D shows the path of the tracks 1830, 1834 with positions of the bosses 1831, 1835 and relative positions of the needle 1814 and stylet 1810 during an actuation cycle. Those of skill in the art will appreciate from this diagram that, by rotating the deployment handle member 1840, a user may advance the stylet 1810 and needle 1804 together and then hold the stylet 1810 longitudinally substantially in place while partially retracting the needle 1814 proximally to deploy a fiducial 1869. To aid understanding, the tracks 1830, 1834 are divided into phases A, B, C, and D, to which reference will be made for describing actuation of the advancement mechanism assembly 1830 for the handle 1800.

During the "phased actuation" depicted diagrammatically in FIG. 18D, the handle 1800 may be actuated, for example, to the position shown in FIG. 18C, where the needle 1814 is extended three units beyond the distal end of the needle sheath 1812 and the handle is rotated. Phase A is shown in two stages. In the first stage, A(1), the stylet boss 1831 and needle boss 1835 are disposed in the proximal end of their respective tracks 1830, 1834. During Phase A, the deployment handle 1840 is rotated, advancing the bosses 1831, 1835 substantially in parallel to the second stage A(2), wherein the needle 1814 and stylet 1810 both advance substantially the same distance distally.

Next, in Phase B, the user continues rotating the deployment handle 1840, whereupon the stylet 1810 is held substantially longitudinally in place (as its track is substantially normal to the longitudinal axis, represented by the vertical axis of FIG. 18D, with the top corresponding to the proximal handle end and the bottom of FIG. 18D to the distal handle end) and the needle 1814 is retracted proximally. This action allows a user to accurately place a fiducial 1869, as the specific location of the distal tip of the needle 1814 and fiducial 1869 can be clearly resolved by radiography and/or ultrasound (particularly if the needle and/or fiducial is echogenic), and the needle 1814 being withdrawn with the stylet holding the fiducial in place preferably will leave the fiducial 1869 substantially in that exact location and orientation. This is shown in FIG. 18C, including the magnified detail inset showing deployment of a fiducial 1869 (which will occur about when the bosses 1831, 1835 are aligned at the line separating Phase B from Phase C in FIG. 18D). It will be appreciated that Phases C and D will substantially repeat Phases A and B, respectively, for successive fiducials as the bosses are advances through the tracks in the direction of the arrow 1899 of FIG. 18D.

Figure 19A:
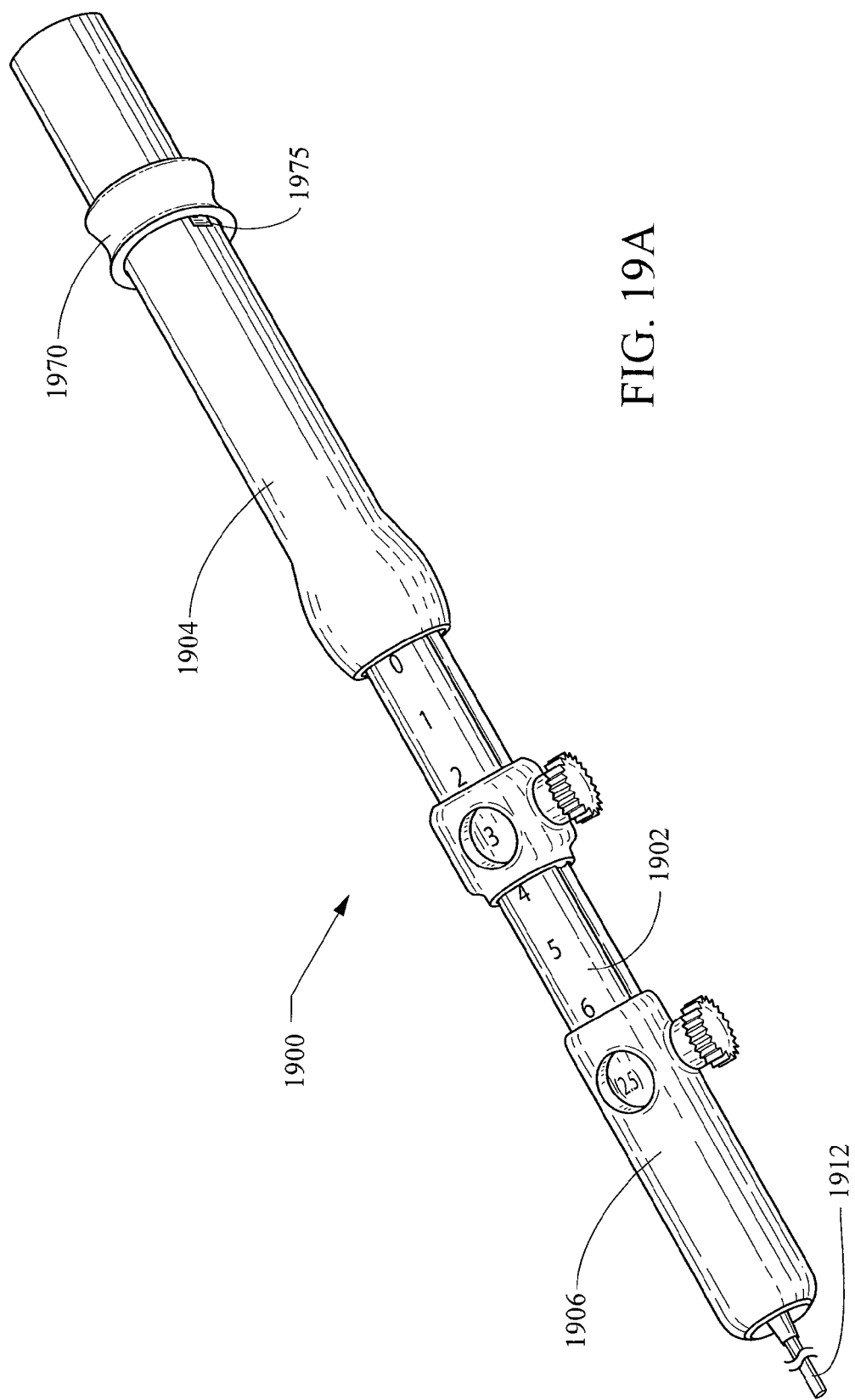
Figure 19B:
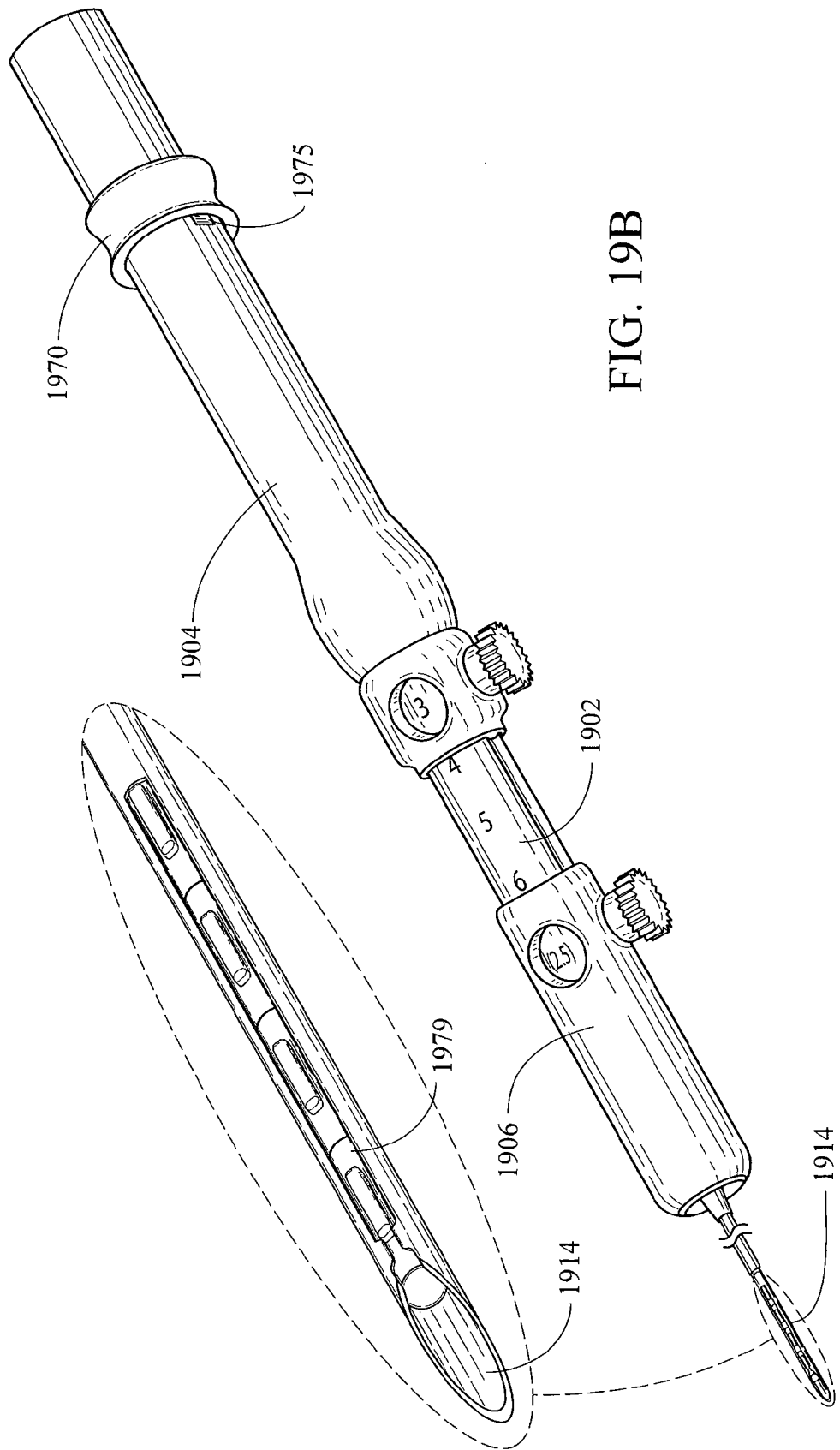

FIGS. 19A-19C show another handle embodiment 1900, using a ratcheted incremental advancement mechanism. As shown in FIG. 19A, the handle 1900 includes a sheath-attached handle member 1902 with a needle-attached handle member 1904 longitudinally slidably disposed on its proximal end. A scope-attachment handle member 1906 is slidably attached to the distal end of the sheath-attached handle member 1902. The sheath-attached handle member 1902 is attached to the needle sheath 1912 and the needle-attached handle member 1904 is attached to the needle 1914 (which may be configured in the manner of any of the needles disclosed herein or later developed in accordance with principles of the present disclosure). A stylet 1910 (visible in FIG. 19C) extends through the needle lumen. The handle 1900 is shown with the needle 1914 extended distally beyond the end of the sheath 1912, and a magnified inset shows an example of a distal needle end with fiducials 1979 awaiting deployment. Each fiducial 1979 includes a protrusion substantially adjacent its proximal end.

The ratcheted incremental advancement mechanism includes an incremental adjustment member 1970 (embodied here as a ring, but configurable in a variety of geometries) is disposed near the proximal end of the needle-attached handle member 1904 with a portion extending through a short longitudinal track 1975. FIG. 19B shows the fiducial deployment system with the handle 1900 actuated to extend the needle 1914 and the stylet 1910 having advanced a distal-most fiducial 1979 beyond the distal tip of the needle.

FIG. 19C is a simplified diagrammatic longitudinal section view of the needle-attached handle 1904 taken along line 19D-19D and illustrating that the stylet 1910 includes a ratcheted surface with periodic ratchet indentations 1921 on one or more sides. The incremental adjustment member 1970 includes at least one pawl 1971 configured to engage the indentations 1921. A keeper pawl 1929 may also be included to help maintain stability and position during actuation. Thus, the incremental adjustment member 1970 includes at least one detent structure 1971 configured to engage one or more complementary detent structures 1921, and any those of skill in the art will appreciate that a variety of detent embodiments may be practiced within the scope of the present invention.

In order to advance a distal fiducial 1979 out of the needle 1914, a user may actuate the incremental adjustment member 1970 by sliding it distally in its track 1975. Distal advancement of the incremental adjustment member 1970 and engagement of the pawl 1971 with the stylet ratchet indentations 1921 pushes the stylet 1910 distally to advance a fiducial 1979 out of the needle lumen as shown in the detail inset of FIG. 19B. The incremental adjustment member 1970 can be slid back to its original position and the process repeated to deploy subsequent fiducials 1979. It should also be appreciated that the needle 1914 may be ratcheted for movement proximally to retract the needle and release a fiducial from its distal tip after that fiducial is in a desired location, within the scope of the present invention. An audible and/or tactile indicia of degree of advancement may be included as noted for other embodiments herein, and the allowed movement of the incremental adjustment member 1970 may be limited by assigning a predetermined length to the track 1975 along which it moves (where, for example, movement fully along that length corresponds to deployment of one fiducial).

Drawings and particular features in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably is used with less invasive endoscopy procedures. It is therefore intended that the foregoing detailed description be regarded as illustrative rather than limiting. And, it should be understood that the following claims, including all equivalents, are intended to define the spirit and scope of this invention.

The invention claimed is:

1. A handle for a fiducial deployment system comprising:
    a first handle member attached to an elongate outer sheath, the outer sheath including a sheath lumen longitudinally disposed therethrough;
    a second handle member disposed longitudinally slidably along the first handle member, the second handle member attached to an elongate needle disposed longitudinally slidably through the sheath lumen, wherein the needle includes a needle lumen disposed longitudinally therethrough;
    a stylet disposed longitudinally slidably through the needle lumen;
    a plurality of at least three separate and independent fiducials disposed in the needle lumen, where each of the fiducials includes a predetermined fiducial body length between end termini of the fiducial; and
    an advancement mechanism attached to a proximal portion of the second handle and to the stylet in a manner configured for effecting longitudinal movement of one of the stylet and the needle relative to the other of the stylet and the needle by predetermined increments, where the predetermined increments are the same distance as the predetermined fiducial body lengths.

2. The handle of claim 1, further comprising a third handle member disposed longitudinally positionable relative to the first handle member and configured for incrementally fixable, longitudinally-adjustable attachment of the first handle member to an external device.

3. The handle of claim 2, wherein the third handle member is configured to attach to a working channel of an endoscope.

4. The handle of claim 1, wherein the advancement mechanism comprises a threaded rotatable advancement member in mechanical communication with the stylet and an anchor member attached to the second handle member, the advancement mechanism configured such that rotation of the advancement member relative to the anchor member will move the stylet longitudinally relative to the second handle member.

5. The handle of claim 4, wherein the rotation is indexed by visual indicia, tactile indicia, audible indicia, or any combination thereof, and wherein said indicia corresponds to a pre-determined longitudinal movement distance of the stylet.

6. The handle of claim 1, wherein the advancement mechanism comprises an advancement member including at least one first detent in mechanical communication with the stylet and an anchor member including at least one second detent attached to the second handle member, the advancement mechanism configured such that a longitudinal movement of the advancement member relative to the anchor member will move the stylet longitudinally relative to the second handle member, and wherein the at least one first detent engages the at least one second detent when longitudinally distally advanced relative to the second handle member by the predetermined increment.

7. The handle of claim 6, wherein the longitudinal movement is indexed by visual indicia, tactile indicia, audible indicia, or a combination thereof, and wherein said indicia corresponds to a known longitudinal movement distance of the stylet.

8. The handle of claim 6, wherein at least one of the first detents or second detents comprises a plurality of detents that engages at least one of the other of the first detents or second detents.

9. The handle of claim 1, further comprising a visual index indicating relative movement of the first and second handle members and indicating extension of the needle relative to the sheath.

10. The handle of claim 1,
    wherein the needle includes
        a tubular cannula body defining the needle lumen and
        a distal needle end region, the distal end region comprising
            a distal needle end opening at a distal end of the needle lumen; and
            at least one generally longitudinal needle slot extending radially through at least a thickness portion of the cannula body and open to the needle lumen, where the needle slot includes at least one detent disposed within and across a width of the needle slot;
    wherein each fiducial comprises
        a generally columnar body including
            a central fiducial portion slidably disposed in the needle lumen; and
            at least one side protuberance projecting into the needle slot; and
    wherein the stylet is configured to advance each fiducial past the at least one detent and out of the distal needle end opening.

11. The handle of claim 10,
    wherein the advancement mechanism comprises a threaded rotatable advancement member in mechanical communication with the stylet and an anchor member attached to the second handle member, the advancement mechanism configured such that a predetermined degree of rotation of the advancement member relative to the anchor member will move the stylet longitudinally distally through the needle by a first of the predetermined increments.

12. The handle of claim 11, wherein the rotation is indexed by visual indicia, tactile indicia, audible indicia, or a combination thereof, and wherein said indicia of rotation corresponds to a known longitudinal movement distance of the stylet.

13. The handle of claim 11, wherein the advancement mechanism is configured such that moving the rotatable advancement member in one direction by the predetermined degree of rotation will advance the stylet distally by the first predetermined increment and will advance a distal-most of the plurality of fiducials past the at least one detent and out of the distal needle end opening.

14. The handle of claim 13, further comprising visual indicia of a distance advanced distally by the stylet and of a number of one or more fiducials advanced past the detent and out of the distal needle end opening.

15. The handle of claim 11, wherein the rotatable advancement member is generally cylindrically shaped.

16. The handle of claim 15, the rotatable advancement member further comprising at least one lateral extension that provides increased rotational leverage.

17. A method of placing a fiducial into a patient body, the method comprising the steps of
   providing the fiducial deployment system handle of claim 13;
   directing the distal needle end through an endoscope to near a first target site in a patient body;
   deploying a fiducial by rotating the rotatable advancement member by the predetermined degree of rotation, thereby pushing the fiducial past the at least one detent surface and into the first target site.

18. The method of claim 17, further comprising the steps of:
   withdrawing the needle proximally from the target site, but not entirely into the endoscope;
   directing the needle to a second target site; and
   repeating the deploying step to deploy another fiducial.

19. A fiducial deployment system comprising:
   a flexible elongate needle sheath configured for passage through a working channel of an endoscope, the needle sheath including
      a sheath lumen extending longitudinally through its length;
   a flexible elongate needle extending slidably through the sheath lumen, the needle including
      a tubular cannula body defining a needle lumen disposed through at least a lengthwise portion of the cannula body and
      a distal needle end region, the distal end region comprising
         a distal needle end opening at a distal end of the needle lumen; and
         at least one generally longitudinal needle slot extending radially through at least a thickness portion of the cannula body and open to the needle lumen, where the needle slot includes at least one detent;
   a plurality of at least three separate and independent fiducials, each including
      a generally columnar body including
         a central fiducial portion slidably disposed in the needle lumen; and
         at least one side protuberance projecting into the needle slot;
   a flexible elongate stylet extending through a portion of the needle lumen and configured to pushingly advance the at least one fiducial past the detent and out of the distal needle end opening; and
   a handle including
      a first handle portion attached to the needle sheath;
      a second handle portion attached to a proximal portion of the needle and slidably attached to the first handle portion, configured such that a longitudinal movement of the second handle portion along the first handle portion slidably moves the needle longitudinally relative to the sheath; and
      a third handle portion including a threaded rotatable advancement member in mechanical communication with the stylet and an anchor member attached to the second handle portion, the advancement member threadedly mounted to the anchor member such that rotation of the advancement member relative to the anchor member by a predetermined, indexed degree of rotation moves the stylet longitudinally relative to the second handle portion by a predetermined lengthwise increment sufficient to advance a distal-most fiducial out of the needle lumen.

20. The fiducial deployment system of claim 19, wherein rotation of the third handle portion is indexed by visual indicia, tactile indicia, audible indicia, or any combination thereof, and wherein said indicia that corresponds to the pre-determined lengthwise increment longitudinal movement distance of the stylet.

* * * * *